(12) United States Patent
Higuchi et al.

(10) Patent No.: US 9,873,675 B2
(45) Date of Patent: Jan. 23, 2018

(54) REACTIVE UV ABSORBER, MAKING METHOD, COATING COMPOSITION, AND COATED ARTICLE

(71) Applicant: SHIN-ETSU CHEMICAL CO., LTD., Tokyo (JP)

(72) Inventors: Koichi Higuchi, Annaka (JP); Yukimasa Aoki, Annaka (JP)

(73) Assignee: SHIN-ETSU CHEMICAL CO., LTD., Tokyo (JP)

( * ) Notice: Subject to any disclaimer, the term of this patent is extended or adjusted under 35 U.S.C. 154(b) by 0 days.

(21) Appl. No.: 15/442,242

(22) Filed: Feb. 24, 2017

(65) Prior Publication Data

US 2017/0298031 A1    Oct. 19, 2017

Related U.S. Application Data

(62) Division of application No. 14/230,816, filed on Mar. 31, 2014, now Pat. No. 9,670,167.

(30) Foreign Application Priority Data

Apr. 1, 2013  (JP) ................................ 2013-075713

(51) Int. Cl.
| | |
|---|---|
| C07D 251/24 | (2006.01) |
| C08K 5/3492 | (2006.01) |
| C08J 7/04 | (2006.01) |
| C09D 4/00 | (2006.01) |
| C08F 222/10 | (2006.01) |

(52) U.S. Cl.
CPC ...... *C07D 251/24* (2013.01); *C08F 222/1006* (2013.01); *C08J 7/047* (2013.01); *C08K 5/3492* (2013.01); *C09D 4/00* (2013.01); *C08J 2369/00* (2013.01); *C08J 2433/10* (2013.01); *Y10T 428/31551* (2015.04); *Y10T 428/31591* (2015.04)

(58) Field of Classification Search
None
See application file for complete search history.

(56) References Cited

U.S. PATENT DOCUMENTS

| | | |
|---|---|---|
| 4,321,400 A | 3/1982 | Ashby |
| 4,555,559 A | 11/1985 | Kimura et al. |
| 4,750,914 A | 6/1988 | Chikaoka et al. |
| 5,322,868 A | 6/1994 | Valet et al. |
| 5,391,795 A | 2/1995 | Pickett |
| 5,990,188 A | 11/1999 | Patel et al. |
| 6,265,576 B1 | 7/2001 | Gupta |
| 8,052,900 B2 | 11/2011 | Fukushima |
| 8,404,349 B2 | 3/2013 | Kita et al. |
| 9,273,213 B2 | 3/2016 | Kostromine |
| 2001/0027231 A1 | 10/2001 | Sugamoto |
| 2010/0221552 A1 | 9/2010 | Ishida |
| 2012/0094127 A1 | 4/2012 | Meyer Zu Berstenhorst et al. |
| 2013/0236743 A1 | 9/2013 | Kostromine et al. |
| 2016/0017169 A1 | 1/2016 | Kostromine |

FOREIGN PATENT DOCUMENTS

| | | |
|---|---|---|
| EP | 1 995 056 A1 | 11/2008 |
| JP | 3-014862 B2 | 2/1991 |
| JP | 3-062177 B2 | 9/1991 |
| JP | 4-214785 A | 8/1992 |
| JP | 6-088065 A | 3/1994 |
| JP | 6-088066 A | 3/1994 |
| JP | 7-278525 A | 10/1995 |
| JP | 9-028785 A | 2/1997 |
| JP | 2000-63701 A | 2/2000 |
| JP | 2010-111715 A | 5/2010 |
| JP | 2010-270230 A | 12/2010 |
| JP | 2012-031434 A | 2/2012 |
| JP | 2012-167288 A | 9/2012 |
| JP | 2012-526159 A | 10/2012 |
| JP | 2012-219102 A | 11/2012 |
| KR | 100454567 B1 | 11/2004 |
| WO | WO 2007/105741 A1 | 9/2007 |
| WO | WO 2010/127805 A1 | 11/2010 |
| WO | WO 2012/049091 A1 | 4/2012 |

OTHER PUBLICATIONS

European Office Communication for European Application No. 14161716.7, dated May 22, 2015.
Extended European Search Report, dated May 26, 2014, for European Application No. 14161716.7.
ProQuest Machine Translation of JP 2000-63701 A, retrieved Oct. 2016.
ProQuest Machine Translation of KR 100454567B1, retrieved Oct. 2016.

*Primary Examiner* — Nicole Buie-Hatcher
(74) *Attorney, Agent, or Firm* — Birch, Stewart, Kolasch & Birch, LLP

(57) ABSTRACT

Novel UV absorbers of benzotriazine type having a plurality of (meth)acryloxy groups have a UV absorbing capacity and a high solubility in multifunctional (meth)acrylate. By combining the (meth)acrylic functional UV absorber with various binder precursors such as photo-curable multifunctional (meth)acrylate, there are obtained coating compositions having improved crosslinking density, UV absorbing capacity, anti-bleeding property, and shelf stability.

3 Claims, 2 Drawing Sheets

REACTIVE UV ABSORBER, MAKING METHOD, COATING COMPOSITION, AND COATED ARTICLE

CROSS-REFERENCE TO RELATED APPLICATION

This application is a Divisional of U.S. patent application Ser. No. 14/230,816 filed on Mar. 31, 2014, which claims priority under 35 U.S.C. § 119(a) to Patent Application No. 2013-075713 filed in Japan on Apr. 1, 2013, the entire contents of which are hereby incorporated by reference.

TECHNICAL FIELD

This invention relates to novel ultraviolet (UV) absorbers, a method for preparing the same, a coating composition comprising the same, and a coated article using the composition.

BACKGROUND ART

Polycarbonate, polymethyl methacrylate and other thermoplastic resin substrates are generally characterized by a number of superior properties including transparency, ductility, high heat distortion temperature, and dimensional stability. Most of these materials are transparent and have long been used as the replacement for glass in many commercial applications. However, these materials may lose transparency because they are readily damaged by scratching and abrasion. Additionally they are susceptible to UV degradation. There thus occur undesired phenomena like substrate yellowing and surface whitening. As one solution to such drawbacks, resin substrates are surface covered with mar resistant coatings having UV absorbers compounded therein.

The mar resistant coatings having UV absorbers compounded therein, however, suffer from the problems that the coatings fail to exert their performance to the full extent because of bleed-out or leaching-out of UV absorbers, and their mar resistance is degraded by compounding of UV absorbers. One prior art approach to overcome these problems is by fixedly binding the UV absorber to the binder component in the mar resistant coating for thereby suppressing any losses of weather resistance and mar resistance due to bleed-out and leaching out. In this approach, the UV absorber must be designed in accordance with the main chain structure and crosslinking mode of the mar resistant coating binder.

For instance, a silicone hard-coat composition comprising a hydrolytic condensate (or precursor) of alkoxysilane has satisfactory mar resistance and durability. The composition is cured via crosslinking reaction by condensation of silanol (SiOH) on the precursor, forming a cured coating. In this silicone hard-coat composition, the UV absorber having a reactive group capable of silanol crosslinking is incorporated, examples of which are known from Patent Documents 1 to 4. However, these reactive silylated UV absorbers suffer from process problems including multiple stages in their synthesis route and removal of hydrosilylation catalyst. In general, a silicone hard-coat film must be laid on a resin substrate via a primer before a tight bond can be achieved between the film and the substrate. Then additional steps including preparation, coating and curing of the primer are necessary.

Another known example of the mar resistant coating is a photo-curable (meth)acrylic coating composition comprising a multifunctional (meth)acrylate and a photopolymerization initiator. Photopolymerization of (meth)acrylic groups in the multifunctional (meth)acrylate induces crosslinking, forming a cured film. In this photo-curable (meth)acrylic coating composition, the UV absorber having a reactive group is incorporated, examples of which are known from Patent Documents 5 to 9. The photo-curable (meth)acrylic coating compositions comprising UV absorbers having a reactive group can be coated and cured to the resin substrates directly without a need for the primer which is essential for the above silicone hard-coat compositions, but still suffer from some outstanding problems.

Patent Documents 5 and 6 disclose alkoxysilyl-containing dibenzoylresorcinol derivatives as the UV absorber having a reactive group. It is believed that cured films have somewhat low mar resistance because the alkoxysilyl group does not participate in crosslinking reaction of photo-curable (meth)acrylic coating. In fact, Patent Documents 5 and 6 refer nowhere to mar resistance. A bleed-out risk is left during long-term weathering, because it is believed that the UV absorbers have not reacted with the binders.

Patent Documents 7 and 8 disclose silsesquioxanes having a (meth)acrylic functional benzotriazole UV-absorbing group. Although these UV absorbers are improved in solubility in multifunctional (meth)acrylate over the unmodified benzotriazole type UV absorbers, they include relatively much portions that do not contribute to UV absorption, like silsesquioxane skeleton. On the assumption that the term "UV-absorbing group content" of a compound refers to a percentage of UV-absorbing groups based on the molecular weight of that compound, these UV absorbers have a low UV-absorbing group content. To gain the necessary UV-absorbing capacity, the amount of the UV absorber loaded is inevitably increased, detracting from certain properties of cured coatings (other than weather resistance) such as mar resistance and adhesion.

Patent Document 9 describes a photo-curable (meth)acrylic polymer having a UV-absorbing group and a (meth)acryloyl group on side chains. This (meth)acrylic polymer reacts with a multifunctional (meth)acrylate in a photo-curable (meth)acrylic coating composition whereby it is fixed within the cured coating. This UV absorber has improved solubility in multifunctional (meth)acrylate, but a low UV-absorbing group content because of polymer form. This suggests that the amount of the absorber loaded must be increased, detracting from mar resistance and adhesion.

On the other hand, (meth)acrylic functional UV absorbers having a relatively low molecular weight and a high UV-absorbing group content are also known. For example, 2-[2'-hydroxy-5'-(methacryloyloxyethyl)phenyl]-2H-benzotriazole is commercially available under the trade name RUVA-93 from Otsuka Chemical Co., Ltd. Also, Patent Documents 10 and 11 describe benzotriazole and benzophenone UV absorbers having an unsaturated double bond linked thereto by a urethane bond via an alkylene chain. Further, benzotriazine UV absorbers having (meth)acrylic functionality bonded thereto are disclosed in Patent Documents 12 to 14. These (meth)acrylic functional UV absorbers of relatively low molecular weight are suitable for the synthesis of (meth)acrylic polymers as in Patent Document 9 because they have only one (meth)acrylic group per molecule, but unfavorable as the UV absorber in photo-curable (meth)acrylic coating compositions because the crosslinking density is reduced, detracting from mar resistance.

In general, UV absorbers of benzophenone and resorcinol type are insufficient in UV absorbing capacity. Some UV absorbers of benzotriazole type are known to be toxic. Those UV absorbers of benzotriazole type devoid of the safety problem are less soluble so that their loading is limited.

In connection with photo-curable (meth)acrylic coating compositions which can be directly applied to resin substrates without a need for primers, (meth)acrylic functional UV absorbers which has both a high solubility in multifunctional (meth)acrylate and a high UV-absorbing group content, and which do not detract from mar resistance and adhesion of cured coatings are unknown.

CITATION LIST

Patent Document 1: JP-B H03-14862
Patent Document 2: JP-B H03-62177
Patent Document 3: JP-A H07-278525
Patent Document 4: JP-A 2012-526159 (WO 2010/127805)
Patent Document 5: U.S. Pat. No. 4,750,914
Patent Document 6: JP-A 2012-167288
Patent Document 7: JP-A 2010-270230
Patent Document 8: JP-A 2012-219102
Patent Document 9: JP-A 2012-031434
Patent Document 10: JP-A H06-88065
Patent Document 11: JP-A H06-88066
Patent Document 12: JP-A H04-214785
Patent Document 13: JP-A H09-028785
Patent Document 14: WO 2007/105741

DISCLOSURE OF INVENTION

An object of the invention is to provide a novel UV absorber of benzotriazine type containing a plurality of (meth)acryloxy groups and having a UV absorbing capacity and a high solubility in multifunctional (meth)acrylate, and a method for preparing the same. Another object is to provide a coating composition comprising the UV absorber which forms a cured coating having mar resistance and adhesion and capable of retaining the UV absorber in a stable manner while preventing bleed-out, and an article covered with a cured coating of the composition.

The inventors have found that UV absorbers having the general formula (1) are novel and can be synthesized through a few steps; and that by combing the UV absorbers as (meth)acrylic functional UV absorber with various binder precursors such as photo-curable multifunctional (meth) acrylates, there are obtained coating compositions having improved crosslinking density, UV absorbing capacity, anti-bleeding property, and shelf stability.

In one aspect, the invention provides a reactive UV absorber, a method for preparing the same, a coating composition comprising the same, and a coated article using the composition, as defined below.

[1] A reactive UV absorber having the general formula (1):

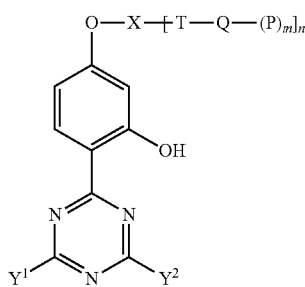

(1)

wherein $Y^1$ and $Y^2$ are each independently a substituent group of the general formula (2):

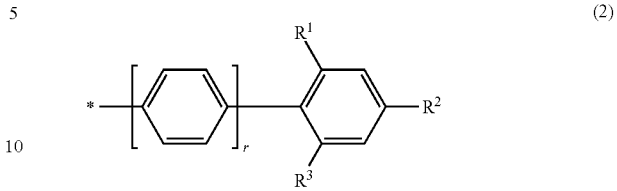

(2)

wherein * stands for a bonding site, r is 0 or 1, $R^1$, $R^2$ and $R^3$ are each independently selected from the group consisting of hydrogen, hydroxyl, $C_1$-$C_{20}$ alkyl, $C_4$-$C_{12}$ cycloalkyl, $C_2$-$C_{20}$ alkenyl, $C_1$-$C_{20}$ alkoxy, $C_4$-$C_{12}$ cycloalkoxy, $C_2$-$C_{20}$ alkenyloxy, $C_7$-$C_{20}$ aralkyl, halogen, —C≡N, $C_1$-$C_5$ haloalkyl, —SO$_2$R', —SO$_3$H, —SO$_3$M (M=alkali metal), —COOR', —CONHR', —CONR'R", —OCOOR', —OCOR', —OCONHR', (meth)acrylamino, (meth)acryloxy, optionally substituted $C_6$-$C_{12}$ aryl and optionally substituted $C_3$-$C_{12}$ heteroaryl, wherein R' and R" are each independently hydrogen, $C_1$-$C_{20}$ alkyl, $C_4$-$C_{12}$ cycloalkyl, optionally substituted $C_6$-$C_{12}$ aryl or optionally substituted $C_3$-$C_{12}$ heteroaryl, X is a di-, tri- or tetravalent, linear or branched, saturated hydrocarbon residue which may be separated by at least one element of oxygen, nitrogen, sulfur, and phosphor, T is a urethane group —O—(C═O)—NH—, Q is a di- or trivalent, linear or branched, saturated hydrocarbon residue which may be separated by at least one element of oxygen, nitrogen, sulfur, and phosphor, P is (meth)acryloxy, m is 1 or 2, and n is an integer of 1 to 3, with the proviso that m and n are not equal to 1 at the same time.

[2] The UV absorber of [1] wherein X is a group having the general formula (3) or (4):

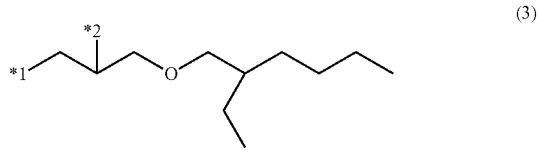

(3)

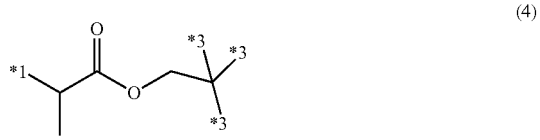

(4)

wherein *1 bonds to the oxygen in formula (1), *2 bonds to T in formula (1), *3 each independently is hydrogen or bonds to T in formula (1) directly or via a divalent, linear or branched, saturated hydrocarbon group which may be separated by at least one element of oxygen, nitrogen, sulfur, and phosphor, at least one *3 bonds to T directly or via a divalent, linear or branched, saturated hydrocarbon group which may be separated by at least one element of oxygen, nitrogen, sulfur, and phosphor, and Q is a group having the general formula (5) or (6):

(5)

-continued (6)

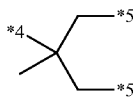

wherein *4 bonds to T in formula (1), and *5 bonds to P in formula (1).

[3] The UV absorber of [2] wherein in formula (1), $R^1$, $R^2$ and $R^3$ are each independently hydrogen or methyl, X is a group of formula (3), Q is a group of formula (6), m is 2, and n is 1.

[4] A method for preparing the reactive UV absorber of any one of [1] to [3], comprising the step (II) of reacting a hydroxyl group bonded to X in a precursor having the following formula (7):

(7)

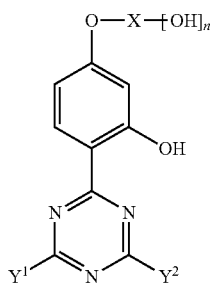

wherein $Y^1$, $Y^2$, X and n are as defined above, with an isocyanate group in a compound having the following formula (8):

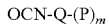

OCN-Q-(P)$_m$        (8)

wherein Q, P and m are as defined above.

[5] The method of [4], further comprising step (I) prior to step (II), provided that X in formula (1) is a group of formula (4) in [2], the step (I) of effecting transesterification between an ester compound having the following formula (9) and a polyhydric alcohol compound having the following formula (10) to form the precursor of formula (7), (9)

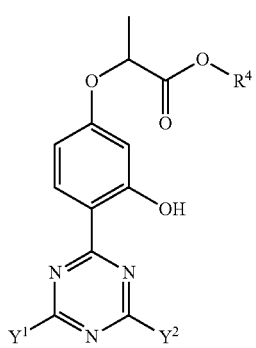

wherein $Y^1$ and $Y^2$ are as defined above, $R^4$ is a monovalent, linear or branched, saturated hydrocarbon group which may be separated by at least one element of oxygen, nitrogen, sulfur, and phosphor, (10)

wherein $R^5$, $R^6$ and $R^7$ are each independently hydrogen, hydroxyl, a monovalent, linear or branched, saturated hydrocarbon group which may be separated by at least one element of oxygen, nitrogen, sulfur, and phosphor, or a monovalent, linear or branched, saturated hydrocarbon group which is terminated with hydroxyl and which may be separated by at least one element of oxygen, nitrogen, sulfur, and phosphor, at least one of $R^5$, $R^6$ and $R^7$ is hydroxyl or a monovalent, linear or branched, saturated hydrocarbon group which is terminated with hydroxyl and which may be separated by at least one element of oxygen, nitrogen, sulfur, and phosphor.

[6] A coating composition comprising the reactive UV absorber of any one of [1] to [3] and a binder precursor.

[7] The coating composition of [6] wherein the binder precursor comprises at least one mono- or multifunctional (meth)acrylate, and the composition further comprises at least one photopolymerization initiator.

[8] The coating composition of [7] wherein the binder precursor comprises at least one member selected from the group consisting of urethane poly(meth)acrylates, and hydrolyzates and hydrolytic condensates of (meth)acryloyl group-containing alkoxysilanes.

[9] The coating composition of [7] or [8] wherein the binder precursor further comprises an organic/inorganic hybrid (meth)acrylate obtained by (co)hydrolytic condensation of colloidal silica and a (meth)acrylic functional alkoxysilane.

[10] The coating composition of any one of [6] to [9], further comprising at least one additive selected from the group consisting of antifouling agents, water repellents, leveling agents, colorants, pigments, tackifiers, IR absorbers, photostabilizers, curing catalysts other than the photopolymerization initiator in [7], metal oxide fine particles other than the organic/inorganic hybrid (meth)acrylate in [9], and UV absorbers other than formula (1) in [1].

[11] A coated article comprising a substrate and a cured coating of the coating composition of any one of [6] to [10] coated on the substrate directly or via another layer of at least one type.

[12] The coated article of [11] wherein the substrate is made of an organic resin or wood.

Advantageous Effects of Invention

UV absorbers of benzotriazine type containing a plurality of (meth)acrylic functional groups and having an improved UV absorbing capacity are novel. They can be synthesized by a simple method. The coating composition comprising the UV absorber is improved in mar resistance by virtue of a high crosslinking density and improved in long-term weather resistance because the cured coating retains the UV absorber therein in a stable manner while preventing the absorber from being bled out.

DESCRIPTION OF PREFERRED EMBODIMENTS

Figure 1:
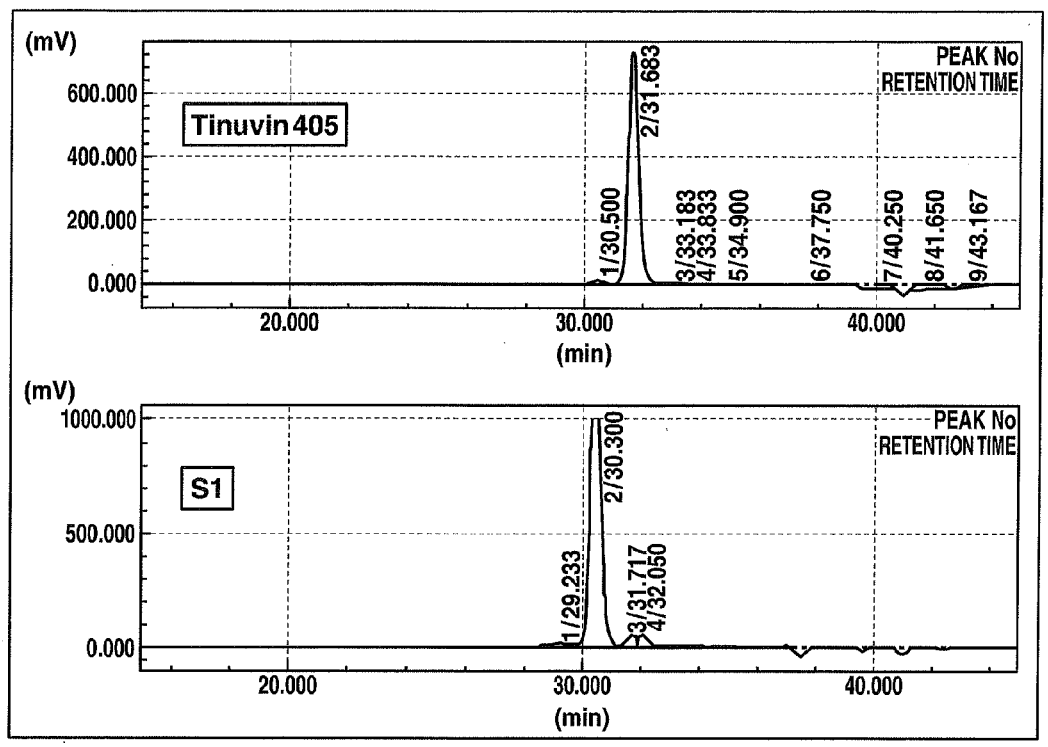
FIG. 1 is a diagram showing the GPC charts of the compound obtained in Example 1 and its reactant.

As used herein, the terminology "(meth)acrylate" refers collectively to acrylate and methacrylate.

Reactive UV Absorber

A first embodiment of the invention is a reactive UV absorber having the general formula (1).

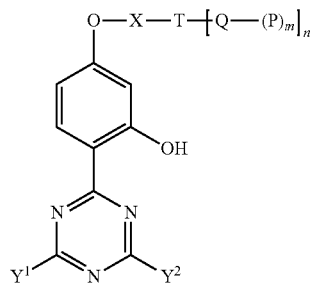
(1)

Herein $Y^1$ and $Y^2$ are each independently a substituent group of the general formula (2).

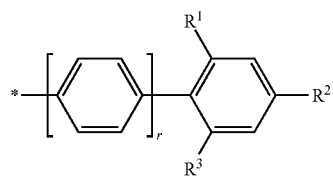
(2)

Herein the asterisk (*) stands for a bonding site, and r is 0 or 1, preferably 1. It is believed that in case of r=1, the radical created upon absorption of UV is stabilized because its conjugated system is expanded.

$R^1$, $R^2$ and $R^3$ are each independently hydrogen, hydroxyl, $C_1$-$C_{20}$ alkyl, $C_4$-$C_{12}$ cycloalkyl, $C_2$-$C_{20}$ alkenyl, $C_1$-$C_{20}$ alkoxy, $C_4$-$C_{12}$ cycloalkoxy, $C_2$-$C_{20}$ alkenyloxy, $C_7$-$C_{20}$ aralkyl, halogen, —C≡N, $C_1$-$C_5$ haloalkyl, —SO$_2$R', —SO$_3$H, —SO$_3$M (M=alkali metal), —COOR', —CONHR', —CONR'R", —OCOOR', —OCOR', —OCONHR', (meth)acrylamino, (meth)acryloxy, $C_6$-$C_{12}$ aryl (optionally substituted with halogen or the like), or $C_3$-$C_{12}$ heteroaryl (optionally substituted with halogen or the like). Of these, hydrogen, hydroxyl, $C_1$-$C_{20}$ alkyl, $C_1$-$C_2$ alkoxy, halogen, and $C_6$-$C_{12}$ aryl are preferred, and hydrogen and $C_1$-$C_{20}$ alkyl are most preferred. R' and R" are each independently hydrogen, $C_1$-$C_{20}$ alkyl, $C_4$-$C_{12}$ cycloalkyl, $C_6$-$C_{12}$ aryl (optionally substituted with halogen or the like) or $C_3$-$C_{12}$ heteroaryl (optionally substituted with halogen or the like). Of these, hydrogen, $C_1$-$C_{20}$ alkyl, and $C_6$-$C_{12}$ aryl are preferred, and hydrogen and $C_1$-$C_{20}$ alkyl are most preferred.

X is a di-, tri- or tetravalent, linear or branched, saturated hydrocarbon residue, typically $C_1$-$C_{20}$ alkyl or $C_4$-$C_{12}$ cycloalkyl, which may be separated by at least one element of oxygen, nitrogen, sulfur, and phosphor. For ease of synthesis and availability of starting reactants, X is preferably a group having the general formula (3) or (4).

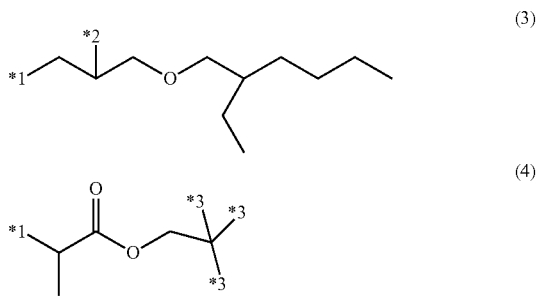

Herein *1 bonds to the oxygen in formula (1), *2 bonds to T in formula (1), *3 each independently is hydrogen or bonds to T in formula (1) directly or via a divalent, linear or branched, saturated hydrocarbon group which may be separated by at least one element of oxygen, nitrogen, sulfur, and phosphor, at least one *3 bonds to T directly or via a divalent, linear or branched, saturated hydrocarbon group which may be separated by at least one element of oxygen, nitrogen, sulfur, and phosphor.

T is a urethane group —O—(C=O)—NH—.

Q is a di- or trivalent, linear or branched, saturated hydrocarbon residue, typically $C_1$-$C_{20}$ alkyl or $C_4$-$C_{12}$ cycloalkyl, which may be separated by at least one element of oxygen, nitrogen, sulfur, and phosphor. For ease of synthesis and availability of starting reactants, Q is preferably a group having the general formula (5) or (6).

Herein *4 bonds to T in formula (1), and *5 bonds to P in formula (1).

P is (meth)acryloxy, specifically a (meth)acryloxy group having the general formula (11):

(11)

wherein $R^8$ is hydrogen or methyl.

The subscript m is 1 or 2, and n is an integer of 1 to 3, with the proviso that m and n are not equal to 1 at the same time. Preferably m is 2 and n is 1.

Shown below are those examples of the reactive UV absorber which are preferred from the aspects of availability of starting reactants, compatibility with relatively highly polar binder precursors such as multifunctional (meth)acrylates, and photo-curability.

(12)
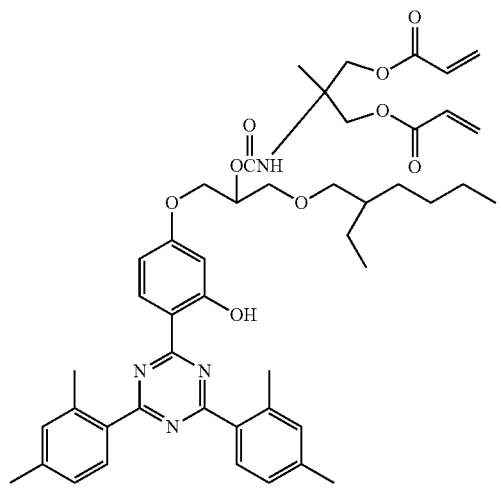
(13)
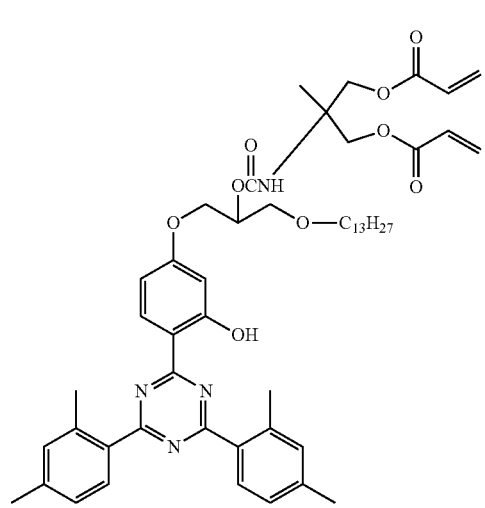
(14)
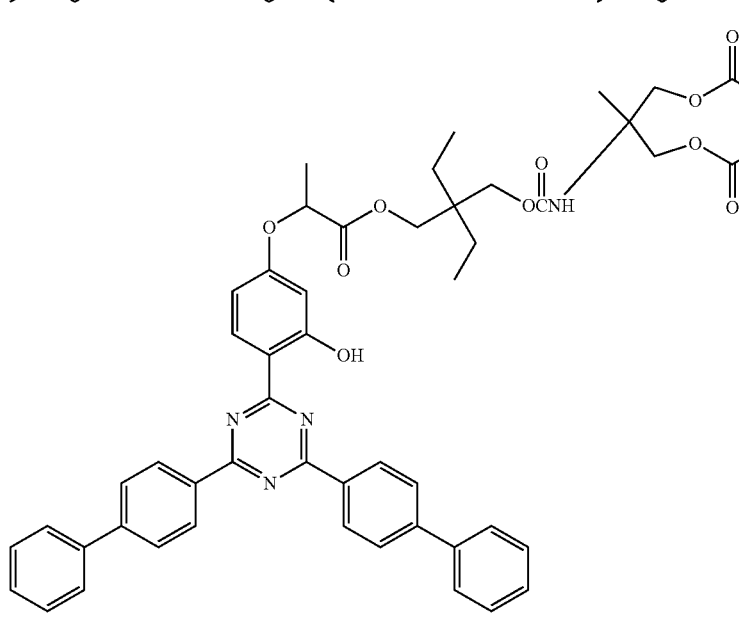
(15)
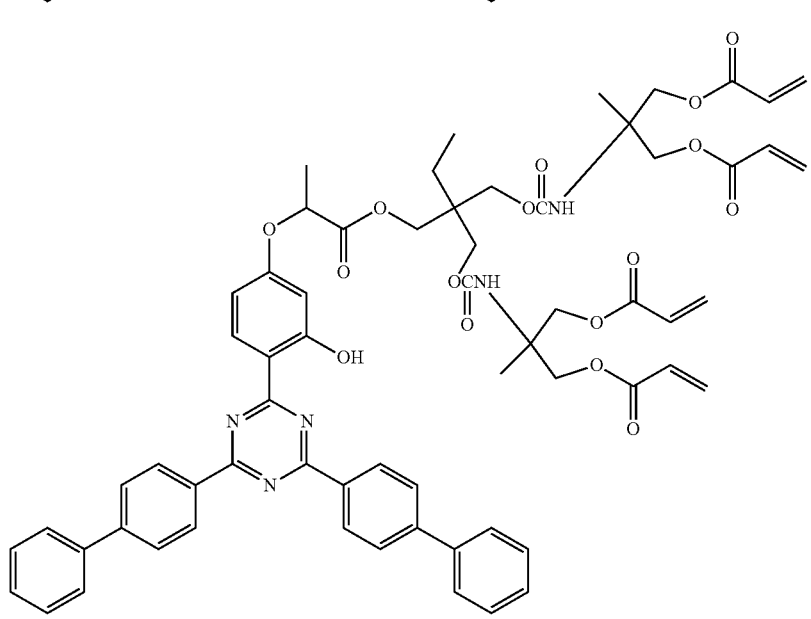

-continued
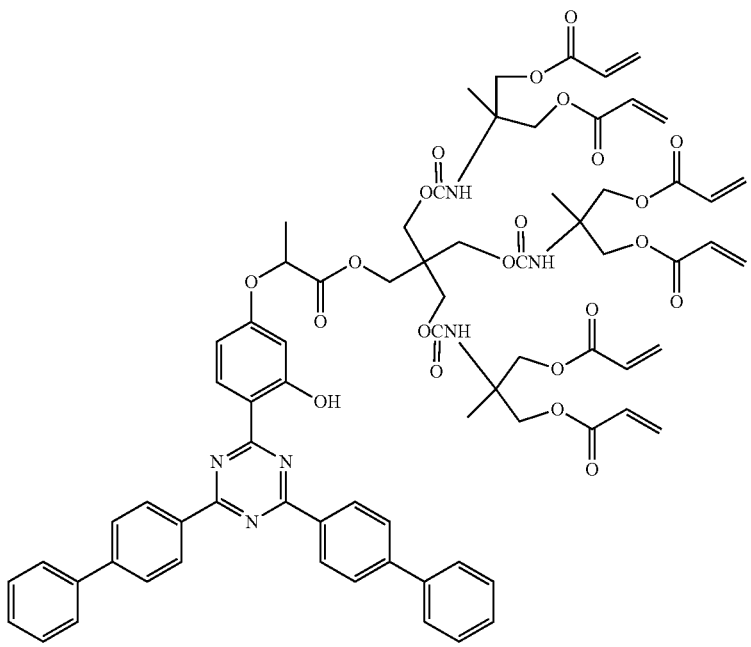
(16)
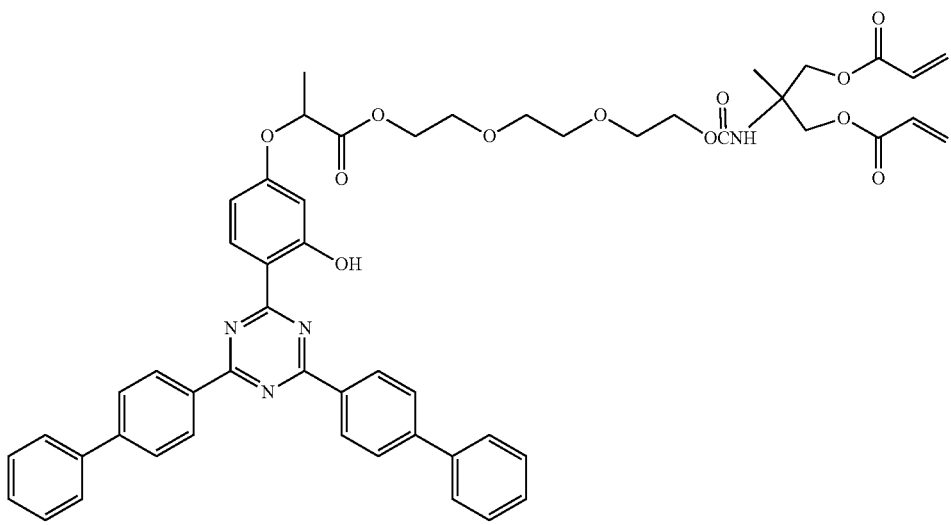
(17)
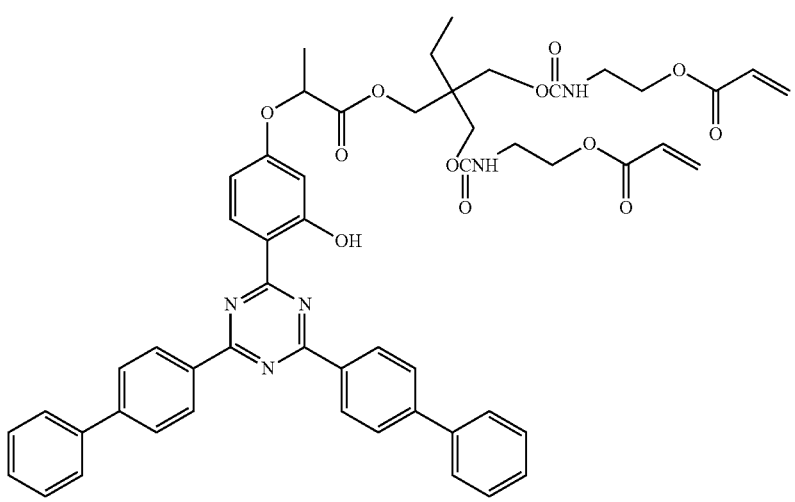
(18)

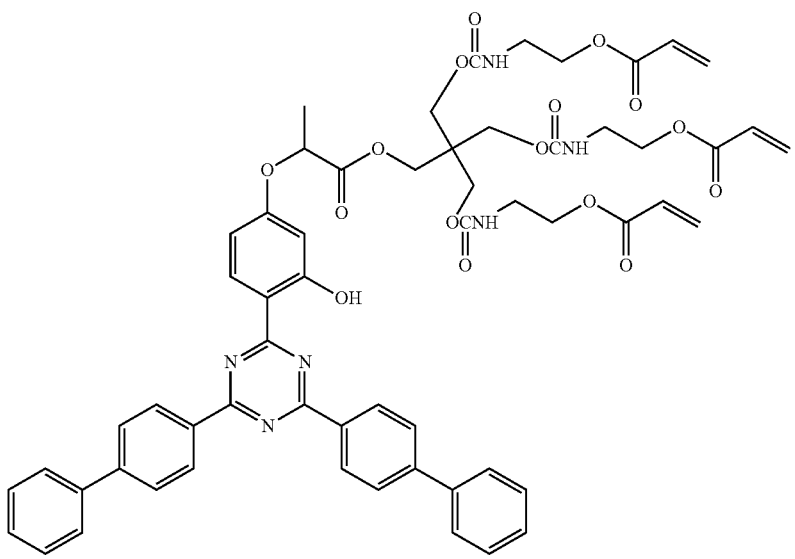
(19)

Preparation of Reactive UV Absorber

The method for preparing the reactive UV absorber is not particularly limited. For example, the absorber may be synthesized by combination of transesterification and urethanating reaction which are both common in the art. The preferred method is described.

A second embodiment is a method for preparing the reactive UV absorber, which starts with a precursor having the following formula (7):

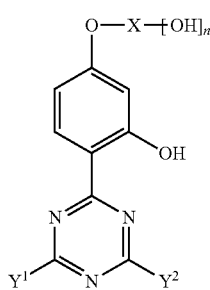
(7)

wherein $Y^1$, $Y^2$, X and n are as defined above.

In a preferred embodiment, those precursors of formula (7) wherein X contains an ester (COO) group, typically of formula (4), are obtained through the step (I) of effecting transesterification between an ester compound of the following formula (9) and a polyhydric alcohol of the following formula (10) to form a precursor of the following formula (7a).

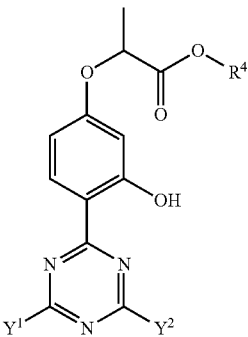
(9)

Herein $Y^1$ and $Y^2$ are as defined above, and $R^4$ is a monovalent, linear or branched, saturated hydrocarbon group which may be separated by at least one element of oxygen, nitrogen, sulfur, and phosphor.

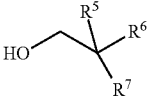
(10)

Herein $R^5$, $R^6$ and $R^7$ are each independently hydrogen, hydroxyl, a monovalent, linear or branched, saturated hydrocarbon group which may be separated by at least one element of oxygen, nitrogen, sulfur, and phosphor, or a monovalent, linear or branched, saturated hydrocarbon group which is terminated with hydroxyl and which may be separated by at least one element of oxygen, nitrogen, sulfur, and phosphor, and at least one of $R^5$, $R^6$ and $R^7$ is hydroxyl or a monovalent, linear or branched, saturated hydrocarbon group which is terminated with hydroxyl and which may be separated by at least one element of oxygen, nitrogen, sulfur, and phosphor.

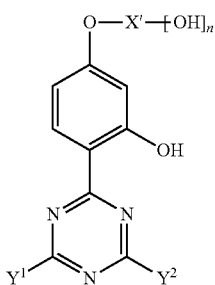

(7a)

Herein $Y^1$, $Y^2$ and n are as defined above, and X' is a di-, tri- or tetravalent, linear or branched, saturated hydrocarbon residue which contains an ester group and which may be separated by at least one element of oxygen, nitrogen, sulfur, and phosphor, typically a group of formula (4).

The target compound of formula (1) is prepared through the step (II) of reacting the precursor of formula (7) with a compound having the following formula (8), specifically reacting a hydroxyl group bonded to X in the precursor of formula (7) with an isocyanate group in the compound of formula (8).

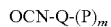  (8)

Herein Q, P and m are as defined above.

Step (I)

Where precursors of formula (7) are known compounds, typically those precursors of formula (7) wherein X is a group of formula (3), they may be prepared by any well-known methods.

Those precursors of formula (7) wherein X contains an ester (COO) group, typically of formula (4), are obtained through the step (I) of effecting transesterification between an ester compound of the following formula (9) and a polyhydric alcohol of the following formula (10) to form a precursor of the following formula (7a).

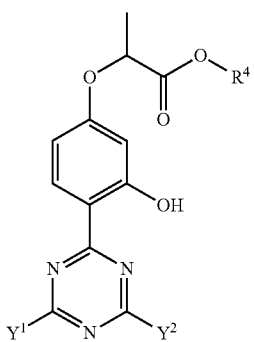

(9)

Herein $Y^1$ and $Y^2$ are as defined above, and $R^4$ is a monovalent, linear or branched, saturated hydrocarbon group which may be separated by at least one element of oxygen, nitrogen, sulfur, and phosphor.

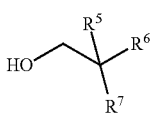

(10)

Herein $R^5$, $R^6$ and $R^7$ are as defined above.

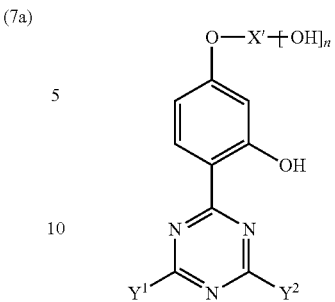

(7a)

Herein $Y^1$, $Y^2$ and n are as defined above, and X' is a di-, tri- or tetravalent, linear or branched, saturated hydrocarbon residue which contains an ester group and which may be separated by at least one element of oxygen, nitrogen, sulfur, and phosphor, typically a group of formula (4).

In formula (9), $R^4$ is a monovalent, linear or branched, saturated hydrocarbon group of 1 to 25 carbon atoms which may be separated by at least one element of oxygen, nitrogen, sulfur, and phosphor. Examples include methyl, ethyl, n-propyl, isopropyl, n-butyl, isobutyl, sec-butyl, tert-butyl, n-pentyl, isopentyl, neopentyl, tert-pentyl, n-hexyl, isohexyl, cyclohexyl, n-heptyl, isoheptyl, n-octyl, 2-ethyl-hexyl, n-nonyl, n-decyl, n-undecyl, and n-dodecyl. Of these, n-octyl is preferred for availability of starting reactants.

The ester compound of formula (9) is commercially available, for example, under the trade name of Tinuvin 479 from BASF.

In formula (10), $R^5$, $R^6$ and $R^7$ are independently hydrogen, hydroxyl, a monovalent, linear or branched, saturated hydrocarbon group which may be separated by at least one element of oxygen, nitrogen, sulfur, and phosphor, or a monovalent, linear or branched, saturated hydrocarbon group which is terminated with hydroxyl and which may be separated by at least one element of oxygen, nitrogen, sulfur, and phosphor, and at least one of $R^5$, $R^6$ and $R^7$ is hydroxyl or a monovalent, linear or branched, saturated hydrocarbon group which is terminated with hydroxyl and which may be separated by at least one element of oxygen, nitrogen, sulfur, and phosphor. Of these, methyl, hydroxyl and methylol are preferred for availability of starting reactants. Suitable polyhydric alcohols include pentaerythritol, trimethylolethane, trimethylolpropane, dimethylolpropane, dimethylolbutane, dimethylolpentane, diethylene glocyol, and triethylene glycol, with pentaerythritol and trimethylolpropane being preferred for availability of starting reactants.

In formula (7a), X' is a di-, tri- or tetravalent, linear or branched, saturated hydrocarbon residue which may be separated by at least one element of oxygen, nitrogen, sulfur, and phosphor, specifically an ester-containing group having a residue derived from the compound of formula (10).

In step (I), the reaction of compounds (9) and (10) is preferably effected at a temperature of 10 to 200° C., more preferably 20 to 180° C. At temperatures below 10° C., the reaction takes a longer time which is undesirable from the aspect of productivity. Temperatures above 200° C. may promote side reactions to form more by-products and sometimes cause the product to be colored.

In step (I), a catalyst may be used to promote the reaction. Any well-known catalysts commonly used in transesterification may be used. For example, tin-based catalysts are suitable. The catalyst is preferably used in an amount of 0 to 5%, more preferably 1,000 ppm to 3% based on the total weight of the compounds (9) and (10). More than 5% of the catalyst tends to form more by-products and cause the product to be colored.

In the practice of reaction, the compounds (9) and (10) are preferably used in equimolar amounts although the amounts are not limited thereto.

A solvent may be used during the reaction of step (I). The preferred solvent is one in which the compound of formula (9) is soluble and which is free of active hydrogen. Use of an active hydrogen-bearing solvent is undesired because by-products other than the precursor of formula (7a) can form. For the purpose of removing water from the reaction system, azeotropic dehydration or dehydration by means of molecular sieves may be carried out. Preferably, the solvent used in step (I) is the same as the solvent used in a coating composition, so that the coating composition can be prepared using the reaction product of step (II) without a need to remove the solvent therefrom.

Step (II)

Step (II) is to react a hydroxyl group bonded to X in the precursor of formula (7) with an isocyanate group in the compound of formula (8) to form the target compound of formula (1).

$$OCN-Q-(P)_m \quad (8)$$

In formula (8), Q is a di- or trivalent, linear or branched, saturated hydrocarbon residue which may be separated by at least one element of oxygen, nitrogen, sulfur, and phosphor, P is (meth)acryloxy, and m is 1 or 2.

Examples of the hydrocarbon residue Q include —CH$_2$—, —CH$_2$CH$_2$—, —CH(CH$_3$)CH$_2$—, —(CH$_2$)$_4$—, —CH(CH$_3$)CH$_2$CH$_2$—, —C(CH$_3$)$_2$CH$_2$—, =CH—, =CHCH$_2$—, =C(CH$_3$)CH$_2$—, —C(CH$_3$)(CH$_2$—)$_2$, etc. Note that the sign "=" designates two valence bonds, but not a double bond.

More preferably Q is a group of formula (5) or (6).

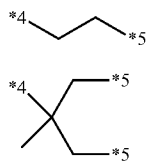

Herein *4 bonds to T in formula (1), and *5 bonds to P in formula (1).

In formula (8), P is (meth)acryloxy, specifically a (meth)acryloxy group having the general formula (11):

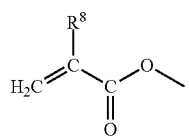

wherein R$^8$ is hydrogen or methyl.

In formula (8), m is 1 or 2, preferably 2. If m exceeds 2, the corresponding compound is difficult to synthesize or not readily available. When n in formula (1) is equal to 1, m is not equal to 1. This is because if m=n=1, the resulting compound of formula (1) becomes a mono(meth)acryloxy compound, that is, monofunctional compound which is incapable of three-dimensional crosslinking, inviting an outstanding loss of mar resistance of the cured coating.

Examples of the compound of formula (8) include 2-acryloyloxyethyl isocyanate, 1,1-bis(acryloyloxymethyl)ethyl isocyanate, and 2-methacryloyloxyethyl isocyanate, which are commercially available under the trade name of Karenz AOI, Karenz BEI, and Karenz MOI from Showa Denko K.K.

In step (II), the reaction of compounds (7) and (8) is preferably effected at a temperature of 10 to 200° C., more preferably 20 to 180° C. At temperatures below 10° C., the reaction takes a longer time which is undesirable from the aspect of productivity. Temperatures above 200° C. may promote side reactions to form more by-products and sometimes cause the product to be colored.

In step (II), a catalyst may be used to promote the reaction. Any well-known catalysts commonly used in urethanating reaction may be used. For example, tin-based catalysts are suitable. The catalyst is preferably used in an amount of 0 to 10,000 ppm, more preferably 100 to 5,000 ppm based on the total weight of the compounds (7) and (8). More than 10,000 ppm of the catalyst tends to form more by-products and cause the product to be colored.

In the practice of reaction, the compounds (7) and (8) are preferably used in equimolar amounts although the amounts are not limited thereto. The amounts may be adjusted in accordance with the number of hydroxyl groups in compound (7) which are available for reaction with the isocyanate group in compound (8). Preferably the ratio of compound (7) to compound (8) is adjusted such that no isocyanate group may be left in the reaction product. If the isocyanate group is left, a coating composition comprising the reaction product tends to lose shelf stability.

Although a hydroxyl group bonded to benzene ring is present in compound (7), this hydroxyl group does not undergo urethanating reaction with the isocyanate group in compound (8). This is probably because reaction of phenolic hydroxyl group with isocyanate group is slow, and the relevant hydroxyl group is crowded in proximity by steric hindrance. In fact, the retention of proton of phenolic hydroxyl group is confirmed by $^1$H-NMR analysis after reaction.

During the urethanating reaction, a polymerization inhibitor such as p-methoxyphenol may be used in order to restrain polymerization of (meth)acryloxy groups. Polymerization may also be restrained by carrying out the reaction in an atmosphere of air or nitrogen containing 4% oxygen. These polymerization restraining means may be used in combination.

A solvent may be used during the reaction of step (II). The preferred solvent is one in which the compound of formula (7) is soluble and which is free of active hydrogen. Use of an active hydrogen-bearing solvent is undesired because it can react with the isocyanate group in compound (8) to form a by-product. For the purpose of removing water from the reaction system, azeotropic dehydration or dehydration by means of molecular sieves may be carried out. Preferably, the solvent used in step (II) is the same as the solvent used in a coating composition, so that the coating composition can be prepared from the reaction product of step (II) without removing the solvent therefrom.

Herein, the term "UV absorbing group content" refers to a proportion of UV absorbing groups per molecular weight of a UV absorber.

Coating Composition

A third embodiment of the invention is a coating composition comprising the reactive UV absorber and a binder precursor.

The binder precursor may be any compound that serves as a coating binder. Examples include thermoplastic resins such as (meth)acrylic resins and polyurethane resins, photocurable (meth)acrylic systems based on mono- and/or multifunctional (meth)acrylate, photo- or heat-curable epoxy systems based on mono- and/or multifunctional epoxy compounds, and heat-curable silicone systems based on silanol compounds. Of these, the photo-curable (meth)acrylic systems based on mono- and/or multifunctional (meth)acrylate are preferred from the aspects of productivity and durability.

The photo-curable (meth)acrylic coating composition using mono- and/or multifunctional (meth)acrylate is specifically a composition comprising (A) the reactive UV absorber defined herein, (B) a mono- and/or multifunctional (meth)acrylate, and (C) a photopolymerization initiator. Various additives may be added as long as the benefits of the invention are not impaired.

Component (A) is preferably used in an amount of 1 to 100 parts, more preferably 5 to 80 parts by weight per 100 parts by weight of component (B). Less than 1 part of component (A) may be insufficient for a coated article to exert satisfactory weather resistance whereas more than 100 parts may detract from the mar resistance and substrate adhesion of a cured coating.

As component (B), any mono- and multifunctional (meth)acrylates may be used as long as they are photo-curable. Suitable (meth)acrylates which can be used herein are mono- or multifunctional (meth)acrylates having a polymerizable unsaturated bond such as, for example, urethane (meth)acrylates, epoxy (meth)acrylates, polyester (meth)acrylates, hydrolyzates and/or condensates of (meth)acryloyloxyalkoxysilanes, and organic/inorganic hybrid (meth)acrylates obtained from hydrolytic condensation of colloidal silica and (meth)acryloyloxyalkoxysilane. A choice may be made among these in accordance with the required properties of a coating.

Examples of suitable monofunctional (meth)acrylates include mono-(meth)acrylates such as methyl (meth)acrylate, ethyl (meth)acrylate, butyl (meth)acrylate, propyl (meth)acrylate, n-butyl (meth)acrylate, isobutyl (meth)acrylate, t-butyl (meth)acrylate, hexyl (meth)acrylate, 2-ethylhexyl (meth)acrylate, lauryl (meth)acrylate, stearyl (meth)acrylate, morpholinyl (meth)acrylate, 2-hydroxyethyl (meth)acrylate, 2-hydroxyproyl (meth)acrylate, 4-hydroxybutyl (meth)acrylate, glycidyl (meth)acrylate, dimethylaminoethyl (meth)acrylate, diethylaminoethyl (meth)acrylate, tricyclodecane (meth)acrylate, polyethylene glycol mono (meth)acrylate, cyclohexyl (meth)acrylate, tetrahydrofurfuryl (meth)acrylate, dicyclopentanyl (meth)acrylate, dicyclopentenyl (meth)acrylate, isobornyl (meth)acrylate, allyl (meth)acrylate, 2-ethoxyethyl (meth)acrylate, benzyl (meth) acrylate, phenoxyethyl (meth)acrylate, phenyl (meth)acrylate; and mono-(meth)acrylate derivatives such as addition products of phthalic anhydride and 2-hydroxyethyl (meth) acrylate.

Examples of suitable multifunctional (meth)acrylates include neopentyl glycol di(meth)acrylate, ethylene glycol di(meth)acrylate, polyethylene glycol (n=2-15) di(meth) acrylate, polypropylene glycol (n=2-15) di(meth)acrylate, polybutylene glycol (n=2-15) di(meth)acrylate, 2,2-bis(4-(meth)acryloxyethoxyphenyl)propane, 2,2-bis(4-(meth) acryloxydiethoxyphenyl)propane, trimethylolpropane diacrylate, bis(2-(meth)acryloxyethyl)-hydroxyethyl isocyanurate, trimethylol propane tri(meth)acrylate, tris(2-(meth)acryloxyethyl) isocyanurate, pentaerythritol tri(meth) acrylate, pentaerythritol tetra(meth)acrylate, dipentaerythritol tetra(meth)acrylate, dipentaerythritol penta(meth) acrylate, dipentaerythritol hexa(meth)acrylate; epoxy poly (meth)acrylates such as epoxy di(meth)acrylate obtained from reaction of bisphenol A diepoxy with (meth)acrylic acid; urethane poly(meth)acrylates such as urethane tri (meth)acrylate obtained from reaction of 1,6-hexamethylene diisocyanate trimer with 2-hydroxyethyl (meth)acrylate, urethane di(meth)acrylate obtained from reaction of isophorone diisocyanate with 2-hydroxypropyl (meth)acrylate, urethane hexa(meth)acrylate obtained from reaction of isophorone diisocyanate with pentaerythritol tri(meth)acrylate, urethane di(meth)acrylate obtained from reaction of dicyclohexyl diisocyanate with 2-hydroxyethyl (meth)acrylate, and urethane di(meth)acrylate obtained by reacting the urethanated reaction product of dicyclohexyl diisocyanate and polytetramethylene glycol (n=6-15) with 2-hydroxyethyl (meth)acrylate; and polyester poly(meth)acrylates such as polyester (meth)acrylate obtained from reaction of trimethylol ethane with succinic acid and (meth)acrylic acid, and polyester (meth)acrylate obtained from reaction of trimethylol propane with succinic acid, ethylene glycol and (meth) acrylic acid. It is noted that "n" used herein designates the number of recurring units in polyethylene glycol and analogues.

Also, hydrolyzates and/or condensates of (meth)acryloyloxyalkoxysilanes, and organic/inorganic hybrid (meth) acrylates obtained from hydrolytic condensation of colloidal silica and (meth)acryloyloxyalkoxysilanes are useful for improving the hardness and durability of a coating. Exemplary are hydrolyzates and hydrolytic condensates of (meth) acryloyl group-containing alkoxysilanes, organic/inorganic hybrid vinyl compounds and organic/inorganic hybrid (meth)acrylates, which are obtained by (co)hydrolytic condensation of a silane (e.g., vinyltrimethoxysilane, vinyltriethoxysilane, p-styryltrimethoxysilane, 3-(meth)acrloxypropylmethyldimethoxysilane, 3-(meth)acryloxypropyltrimethoxysilane, 2-(meth)acryloxyethyltrimethoxysilane, 2-(meth)acryloxyethyltriethoxysilane, (meth)acryloxymethyltrimethoxysilane, (meth)acryloxymethyltriethoxysilane, 3-(meth)acryloxypropylmethyldiethoxysilane, 3-(meth)acryloxypropyltriethoxysilane, 8-(meth)acryloxyoctyltrimethoxysilane or 8-(meth)acryloxyoctyltriethoxysilane) alone or in admixture with another silane, optionally in the presence of colloidal silica.

If desired, a plurality of the above-exemplified compounds may be used in combination as component (B), with such a combination being preferred. In particular, combinations of one or two multifunctional (meth)acrylates with a urethane poly(meth)acrylate compound having at least two radical polymerizable unsaturated double bonds per molecule and/or a hydrolyzate or hydrolytic condensate of (meth)acryloyl group-containing alkoxysilane are preferred. Among others, combinations of two or more of hexane diol di(meth)acrylate, poly(meth)acrylate of mono- or polypentaerythritol, urethane poly(meth)acrylate having at least two radical polymerizable unsaturated double bonds per molecule, and poly[(meth)acryloyloxyalkyl] (iso)cyanurate, (co)hydrolyzate/condensate of (meth)acryloyloxypropylalkoxysilane alone or in admixture with another silane, and organic/inorganic hybrid (meth)acrylate obtained by (co) hydrolytic condensation of colloidal silica and a (meth) acrylic functional alkoxysilane such as (meth)acryloyloxypropylalkoxysilane alone or in admixture with another silane are more preferred because coatings having improved heat resistance, chemical resistance, durability and adhesion to substrates are obtainable.

Component (C) is a photopolymerization initiator which is not particularly limited and may be selected in consideration of compatibility and curability in the photo-curable coating composition.

Examples of the initiator (C) include carbonyl compounds such as benzoin, benzoin monomethyl ether, benzoin isopropyl ether, acetoin, benzyl, benzophenone, p-methoxybenzophenone, diethoxyacetophenone, benzyl dimethyl ketal, 2,2-diethoxyacetophenone, 1-hydroxycyclohexyl phenyl ketone, methyl phenyl glyoxylate, and 2-hydroxy-2-methyl-1-phenylpropan-1-one; sulfur compounds such as tetramethylthiuram monosulfide and tetramethylthiuram disulfide; phosphoric acid compounds such as 2,4,6-trimethylbenzoyldiphenylphosphine oxide, 2,4,6-trimethylbenzoylphenylethoxyphosphine oxide, bis(2,4,6-trimethylbenzoyl)phenylphosphine oxide, and bis(2,6-dimethoxybenzoyl)-2,4,4-trimethylpentylphosphine oxide; 2-benzyl-2-dimethylamino-1-(4-morpholinophenyl)butanone-1 and camphorquinone. These compounds may be used alone or in admixture of two or more. Any two or more of them may be combined in accordance with the required properties of coatings.

Component (C) is preferably used in an amount of 0.1 to 10 parts, more preferably 1 to 8 parts by weight per 100 parts by weight of components (A) and (B) combined. With less than 0.1 part of component (C), the resulting coating may experience a noticeable drop of cure speed and losses of mar resistance and substrate adhesion. With more than 10 parts of component (C), a cured coating may be colored or degraded in weather resistance.

If desired, the coating composition comprising the reactive UV absorber as component (A) may further contain one or more additives. Suitable additives include UV absorbers other than component (A), organic solvents, antifouling agents, water repellents, leveling agents, colorants, pigments, antioxidants, anti-yellowing agents, bluing agent, defoamers, thickeners, anti-settling agents, antistatics, surfactants, tackifiers, IR absorbers, photostabilizers, curing catalysts, and metal oxide fine particles. Preferably, the coating composition comprises at least one additive selected from among antifouling agents, water repellents, leveling agents, colorants, pigments, tackifiers, IR absorbers, photostabilizers, curing catalysts other than the photopolymerization initiator, metal oxide fine particles other than the above-said organic/inorganic hybrid (meth)acrylate (which may be referred as colloidal silica surface-treated with a (meth)acrylic functional alkoxysilane hereinafter), and UV absorbers other than component (A).

Any suitable organic solvent may be selected in accordance with a particular application method. For example, a choice may be made from alcohol solvents such as isobutanol, glycol solvents such as propylene glycol monomethyl ether, ester solvents such as n-butyl acetate, ketone solvents such as methyl isobutyl ketone, and aromatic solvents such as toluene, and any one or more of them are used in such amounts that the coating composition may have a viscosity of up to 20 mPa·s where spray coating is employed, or a viscosity of up to 100 mPa·s where shower flow coating or dipping is employed.

In the case of high-solids type coating compositions having a solid content in excess of 80% by weight, the solvent should be carefully selected while taking into account the solubility of additives.

The thickness of a coating of the coating composition is not particularly limited, but typically 0.1 to 50 μm. Preferably the coating thickness is 1 to 30 μm because such coating meets the desired properties including hardness, mar resistance, long-term stable adhesion and crack resistance. If the thickness is less than 0.1 μm, the coating may be defective or fail to impart satisfactory UV absorbing capacity. A coating with a thickness in excess of 50 m tends to crack.

The substrate used herein is not particularly limited. Included are organic resins such as plastic molded parts, wood parts, fibers or fabrics, ceramics, glass, metals and composite products thereof. Suitable plastic materials, of which substrates are made, include polycarbonate resins, polystyrene resins, acrylic resins, modified acrylic resins, urethane resins, thiourethane resins, polycondensates of halogenated bisphenol A with ethylene glycol, acrylic urethane resins, halogenated aryl group-containing acrylic resins, sulfur-containing resins, polyalkylene terephthalate resins, cellulose resins, amorphous polyolefin resins, and composite resins thereof. Also useful are such resin substrates which have been surface treated, for example, by chemical treatment, corona discharge treatment, flame treatment, plasma treatment, acid or alkaline treatment, as well as laminates consisting of a substrate and a surface layer of different resins. Exemplary laminates include laminates of a polycarbonate resin substrate and a surface layer of acrylic resin or urethane resin, and laminates of a polyester resin substrate and a surface layer of acrylic resin, which are manufactured by co-extrusion or laminating techniques.

The coating composition may be applied to the surface of a substrate directly or via an undercoat if desired. Suitable undercoats include a primer layer, UV absorbing layer, printed layer, recording layer, heat-ray shielding layer, tacky layer, and inorganic evaporated film.

Also, if desired, an overcoat may be applied onto the cured coating of the coating composition. Suitable overcoats include an adhesive layer, UV absorbing layer, printed layer, recording layer, heat-ray shielding layer, tacky layer, inorganic evaporated film, water or oil repellent layer, and hydrophilic anti-fouling layer.

The coating composition of the present invention imparts excellent mar resistance. In this case, in order to further improve mar resistance, inorganic evaporated film can be covered on the cured coating of the coating composition. The inorganic evaporated film is not restricted so long as the film is formed by a dry film-forming method. Examples of the inorganic evaporated films include films mainly composed of metals, metal oxides, metal nitrides, and metal sulfides. The metal is at least one element selected from Si, Ti, Zn, Al, Ga, In, Ce, Bi, Sb, B, Zr, Sn and Ta. Diamond-like carbon films having a high hardness and excellent insulating property are also exemplified. The film laminating method is not limited if the inorganic evaporated film is formed by dry film-forming method including a physical gaseous phase technique such as resistance heating deposition, electron beam deposition, molecular-beam epitaxy, ion beam deposition, ion plating and sputtering, and chemical gaseous phase technique such as thermal CVD, plasma CVD, light CVD, epitaxial CVD, atomic layer CVD and Cat-CVD.

A coated article comprising a substrate covered with a cured coating of the coating composition exhibits improved mar resistance, UV absorption, heat resistance, water resistance and bleed resistance.

Once the coating composition comprising the reactive UV absorber as component (A) is coated onto a substrate, it is cured by application of heat and/or light. Photo-cure is advantageous for productivity. One typical photo-cure process involves coating the coating composition onto a substrate in such a buildup as to achieve the desired film thickness, allowing the solvent to volatilize off, and irradiating UV or electron beam using high-pressure mercury lamps, metal halide lamps, LED lamps or the like. The atmosphere of irradiation may be air or an inert gas such as nitrogen or argon.

More specifically, the coating composition is applied on the substrate with the conventional application method such as brushing, spraying, immersion, flow coating, roll coating, curtain coating, spin coating, and knife coating.

After application, the coating may be dried. The drying condition is not restricted so long as the solvent can be removed, although the drying is generally conducted by heating the substrate at a heat-resistant temperature of the substrate, for example, at a temperature of 15 to 120° C. for 1 to 20 minutes.

The coating is cured preferably by application of light. Although the irradiation source and the irradiation dose are not limited, the irradiating source may include low-pressure, middle-pressure, high-pressure or ultra high-pressure mercury lamps, chemical lamps, carbon arc lamps, xenon lamps, metal halide lamps, fluorescent lamps, tungsten lamps, and sun light, and the irradiation dose is preferably 10 to 10,000 $mJ/cm^2$, more preferably 300 to 5,000 $mJ/cm^2$ The reactive UV absorber of the invention is desirably used as a photo-curable coating composition intended for outdoor use. The photo-curable coating composition is typically applied onto the surface of automobile headlamp lenses, vehicle sensors, and resin glass. Such substrates are often made of polycarbonate because polycarbonate has a good balance of impact resistance, heat resistance, transparency and lightweight. However, polycarbonate is short in chemical resistance, weather resistance, and mar resistance. For this reason, it is desired to coat polycarbonate substrates with the inventive coating composition.

Coating of polycarbonate substrates with the inventive coating composition is effective for preventing the polycarbonate from yellowing and surface degradation. The coated article has a surface hardness as high as glass, and meets lightweight and ease of molding. Thus the coated article finds a wide variety of uses as automobile headlamp lenses, vehicle sensors, vehicle windows, outdoor signboards, green house or building glazing, terrace or garage roofs, balconies, and meter covers.

EXAMPLE

Examples of the invention are given below by way of illustration and not by way of limitation. In Examples, all parts and percentages are by weight unless otherwise indicated. Mw is a weight average molecular weight as measured by GPC versus polystyrene standards. GPC stands for gel permeation chromatography, $^1$H-NMR for proton nuclear magnetic resonance spectroscopy, and IR for infrared absorption spectroscopy.

GPC Analysis Conditions
Instrument: HLC-8320 GPC by Tosoh Corp.
Column: TSKgel G4000HXL+G3000HXL+G2000HXL+G2000HXL (each inner diameter 6 mm, length 150 mm) by Tosoh Corp.
Eluent: tetrahydrofuran
Column oven temperature: 40° C.
Flow rate: 1 mL/min
Detector: refractive index (RI) detector
Standards: monodisperse polystyrene
$^1$H-NMR Analysis Conditions Instrument: AVANCE III 400 by Bruker Corp.
Solvent: $CDCl_3$
Internal standard: tetramethylsilane (TMS)
IR Analysis Conditions
Instrument: Nicolet 6700 by Thermo Fisher Synthesis of Reactive UV Absorbers Example 1

Figure 2:
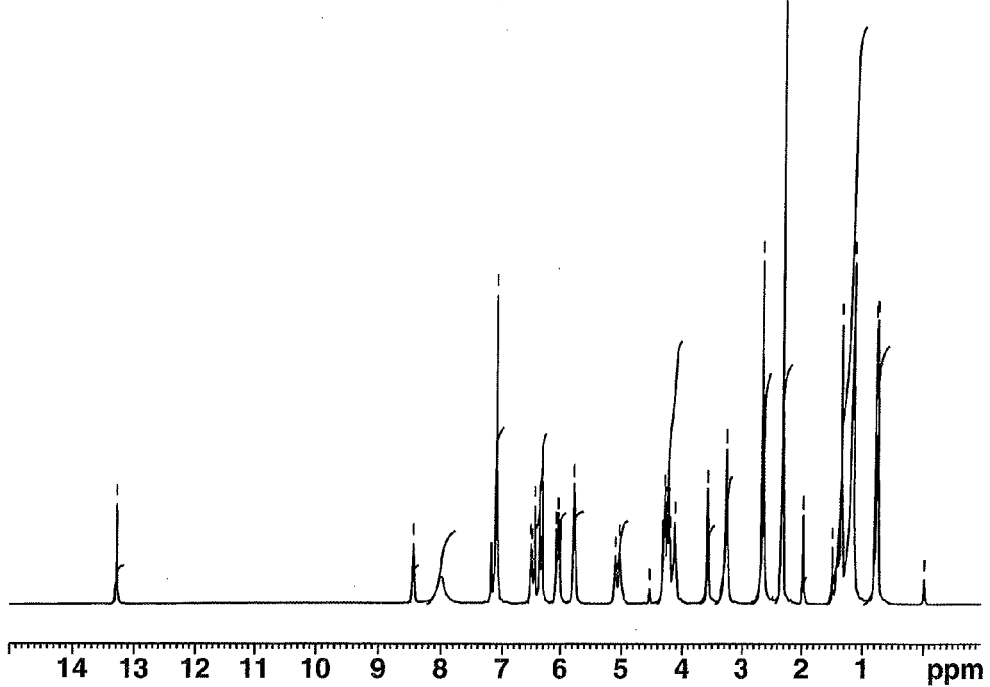
FIG. 2 illustrates the $^1$H-NMR chart of the compound obtained in Example 1.
Figure 3:
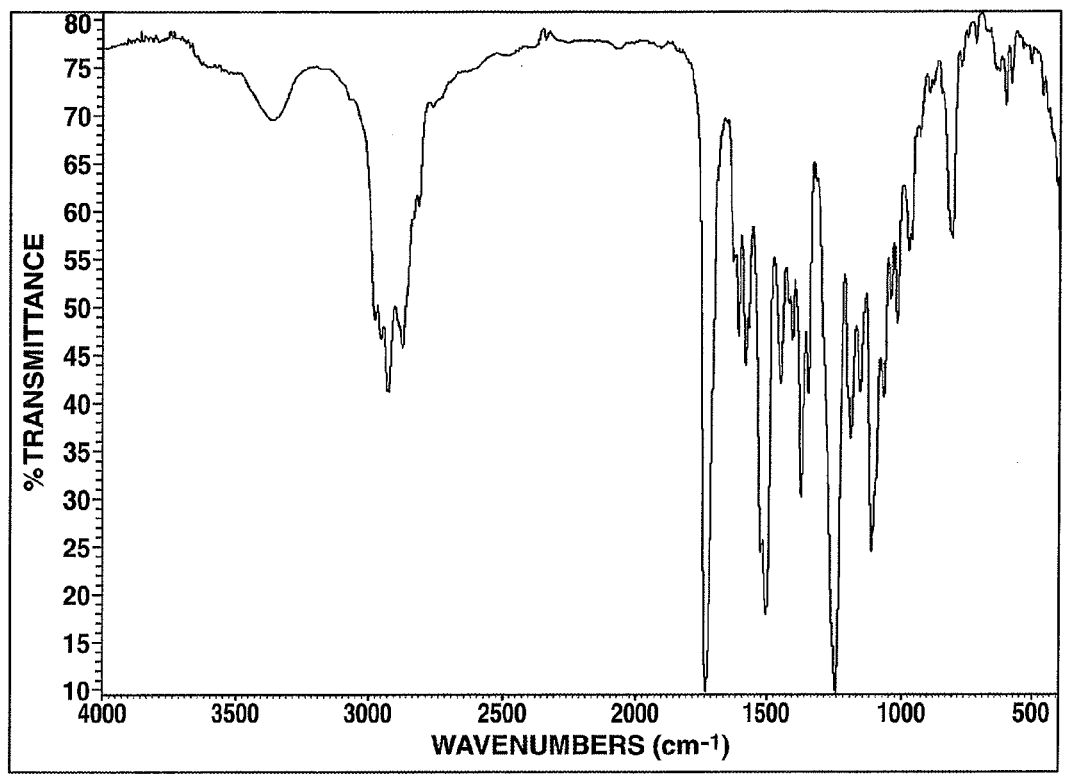
FIG. 3 illustrates the IR chart of the compound obtained in Example 1.

A 1-L flask was charged with 87.6 g (0.15 mol) of Tinuvin 405 (BASF, 2-[4-[(2-hydroxy-3-(2'-ethyl)hexyl)oxy]-2-hydroxyphenyl]-4,6-bis(2,4-dimethylphenyl)-1,3,5-triazine), 391.5 g of propylene glycol monomethyl ether acetate, and 0.12 g of methoxyphenol, which were heated and stirred at 80° C. in a 4% oxygen/nitrogen atmosphere. To the flask, 35.9 g (0.15 mol) of Karenz BEI (Showa Denko K.K., 1,1-bis(acryloyloxymethyl)ethyl isocyanate) and 0.12 g of dioctyltin oxide were added, followed by reaction at 80° C. for hours. The reaction solution was cooled to room temperature, passed through a silica gel-loaded column, and concentrated in vacuum, obtaining 110.8 g of a yellow clear viscous liquid. From the analysis results including GPC (FIG. 1), $^1$H-NMR (FIG. 2), and IR (FIG. 3), this liquid was identified to be a compound S1 of the following formula (12). The compound S1 has a UV absorbing group content of 48% as calculated from formula (12).

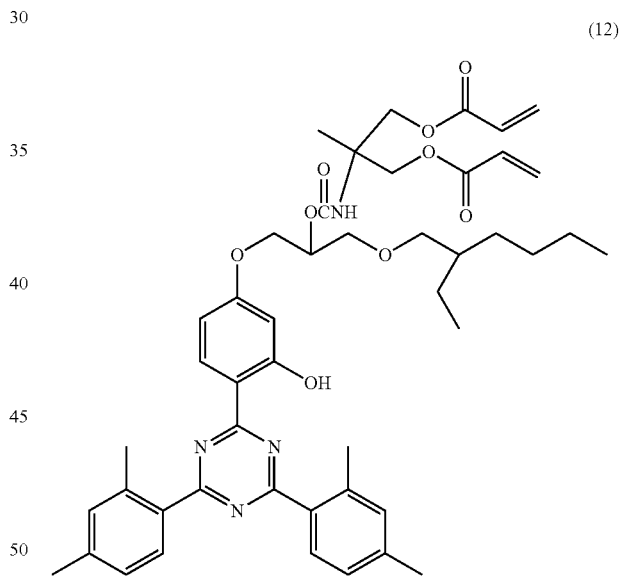

(12)

Example 2

A 1-L flask was charged with 115 g (active ingredient 85%, 0.15 mol calculated from solids) of Tinuvin 400 (BASF, 2-[4-{(hydroxy-3-dodecyloxypropyl)oxy}-2-hydroxyphenyl]-4,6-bis(2,4-dimethylphenyl)-1,3,5-triazine), which was concentrated in vacuum to remove the volatiles. The flask was cooled to room temperature and further charged with 391.5 g of propylene glycol monomethyl ether acetate and 0.12 g of methoxyphenol, which were heated and stirred at 80° C. in a 4% oxygen/nitrogen atmosphere. To the flask, 35.9 g (0.15 mol) of Karenz BEI (Showa Denko K.K., 1,1-bis(acryloyloxymethyl)-ethyl isocyanate) and 0.12 g of dioctyltin oxide were added, followed by reaction at 80° C. for 5 hours. The reaction solution was cooled to room temperature, passed through a silica gel-loaded column, and concentrated in vacuum, obtaining 120.3 g of a compound S2 of the following formula (13). The compound S2 has a W absorbing group content of 44% as calculated from formula (13).

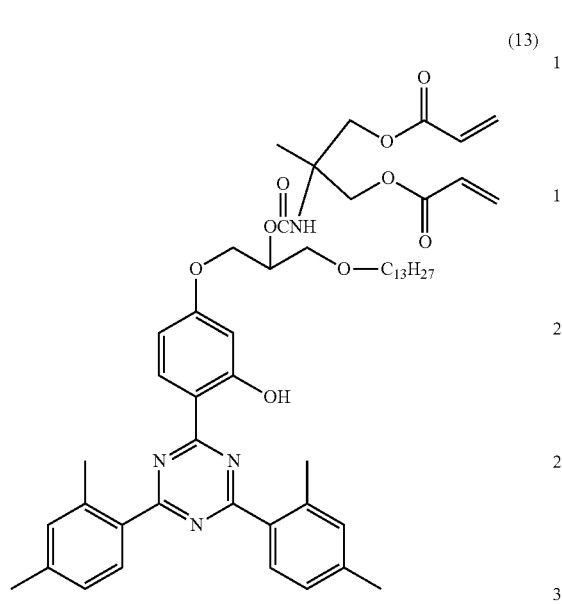

(13)

Example 3

A 1-L flask was charged with 101.7 g (0.15 mol) of Tinuvin 479 (BASF, 2-[2-hydroxy-4-(1-octyloxycarbonylethoxy)-phenyl]-4,6-bis(4-phenylphenyl)-1,3,5-triazine), 220 g of 1,1,1-tris(hydroxymethyl)propane, and 8 g of dioctyltin oxide, which were heated and stirred at 165° C. for 5 hours in a nitrogen atmosphere. The reaction solution was cooled to room temperature and crystallized from methanol. The crystals were filtered and washed with methanol. This was followed by recrystallization from toluene, obtaining a precursor having the following formula (20).

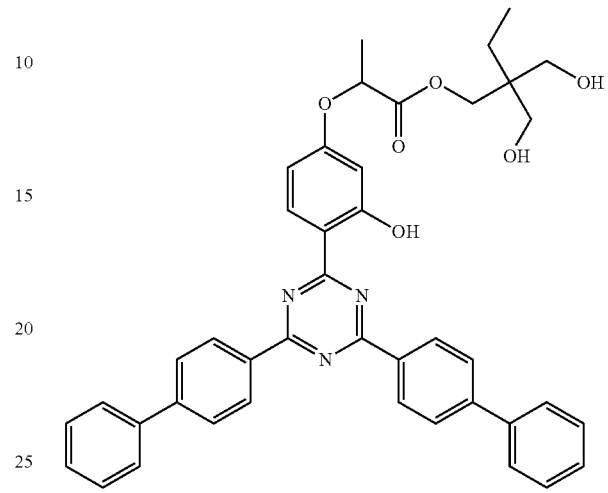

(20)

Next, a 500-mL flask was charged with 35 g (0.05 mol) of the precursor of formula (20), 130.5 g of propylene glycol monomethyl ether acetate, and 0.04 g of methoxyphenol, which were heated and stirred at 80° C. in a 4% oxygen/nitrogen atmosphere. To the flask, 24 g (0.1 mol) of Karenz BEI (Showa Denko K.K., 1,1-bis(acryloyloxymethyl)ethyl isocyanate) and 0.04 g of dioctyltin oxide were added, followed by reaction at 80° C. for 5 hours. The reaction solution was cooled to room temperature, passed through a silica gel-loaded column, and concentrated in vacuum, obtaining 41.8 g of a compound S3 having the following formula (15). The compound S3 has a UV absorbing group content of 41% as calculated from formula (15).

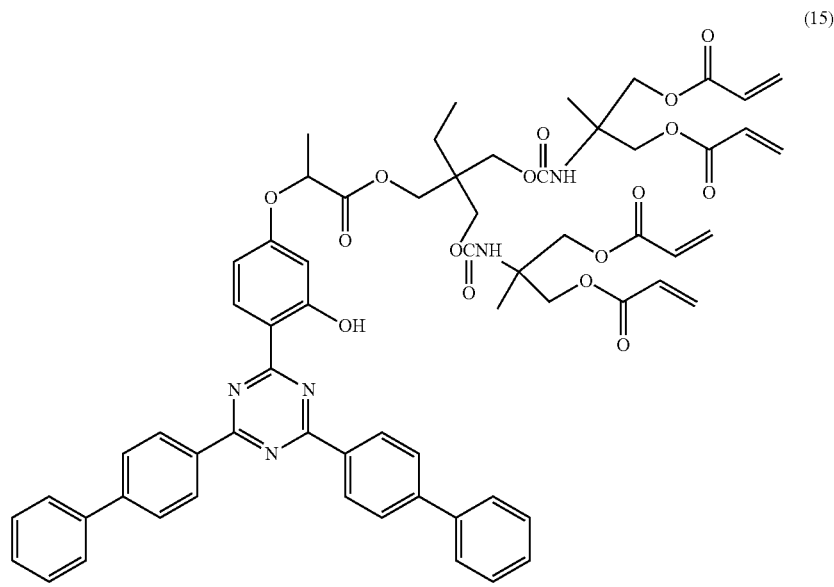

(15)

Example 4

A 1-L flask was charged with 101.7 g (0.15 mol) of Tinuvin 479 (BASF, 2-[2-hydroxy-4-(1-octyloxycarbonylethoxy)-phenyl]-4,6-bis(4-phenylphenyl)-1,3,5-triazine), 250 g of 1,3-dimethyl-3,4,5,6-tetrahydro-2-pyrimidinone, 250 g of pentaerythritol, and 8 g of dioctyltin oxide, which were heated and stirred at 165° C. for 5 hours in a nitrogen atmosphere. The reaction solution was cooled to room temperature and crystallized from methanol. The crystals were filtered and washed with methanol. This was followed by recrystallization from toluene, obtaining a precursor having the following formula (21).

Next, a 500-mL flask was charged with 35 g (0.05 mol) of the precursor of formula (21), 130.5 g of propylene glycol monomethyl ether acetate, and 0.04 g of methoxyphenol, which were heated and stirred at 80° C. in a 4% oxygen/nitrogen atmosphere. To the flask, 21.3 g (0.15 mol) of Karenz AOI (Showa Denko K.K., 2-acryloyloxyethyl isocyanate) and 0.04 g of dioctyltin oxide were added, followed by reaction at 80° C. for 5 hours. The reaction solution was cooled to room temperature, passed through a silica gel-loaded column, and concentrated in vacuum, obtaining 39.1 g of a compound S4 having the following formula (19). The compound S4 has a UV absorbing group content of 43% as calculated from formula (19)

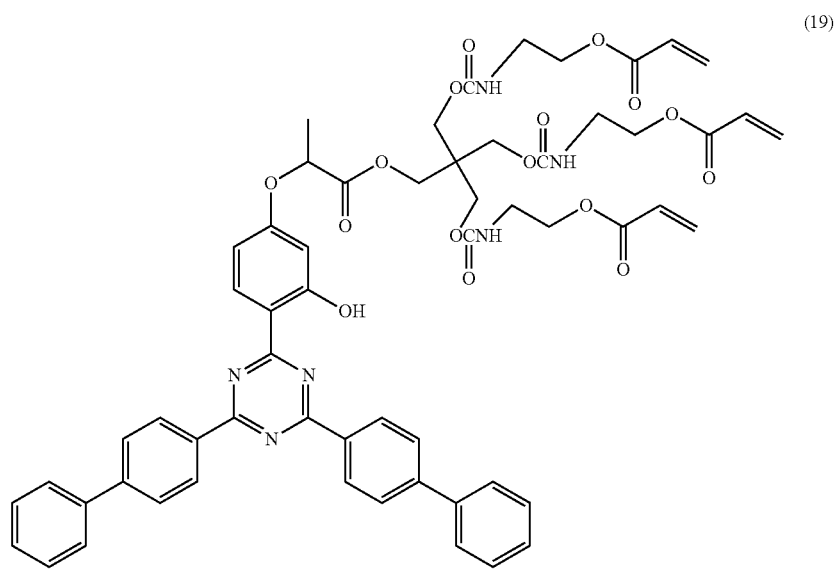

(19)

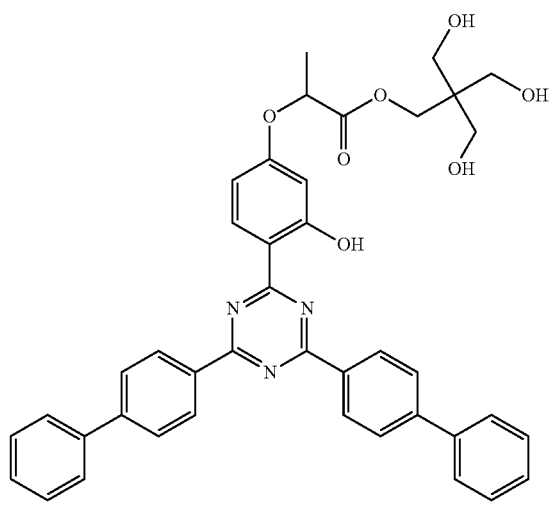

(21)

Synthesis of Other UV Absorbers

Reference Example 1

(UV Absorber Having One Methacryloxy Group)

A 500-mL flask was charged with 29.2 g (0.05 mol) of Tinuvin 405 (BASF, 2-[4-[(2-hydroxy-3-(2'-ethyl)hexyl)oxy]-2-hydroxyphenyl]-4,6-bis(2,4-dimethylphenyl)-1,3,5-triazine), 130 g of propylene glycol monomethyl ether acetate, and 0.04 g of methoxyphenol, which were heated and stirred at 80° C. in a 4% oxygen/nitrogen atmosphere. To the flask, 7.8 g (0.05 mol) of Karenz MOI (Showa Denko K.K., 2-methacryloyloxyethyl isocyanate) and 0.04 g of dioctyltin oxide were added, followed by reaction at 80° C. for 5 hours. The reaction solution was cooled to room temperature, passed through a silica gel-loaded column, and concentrated in vacuum, obtaining 34.3 g of a compound T405MOI having the following formula (22). The compound T405MOI has a U absorbing group content of 53% as calculated from formula (22).

(19)

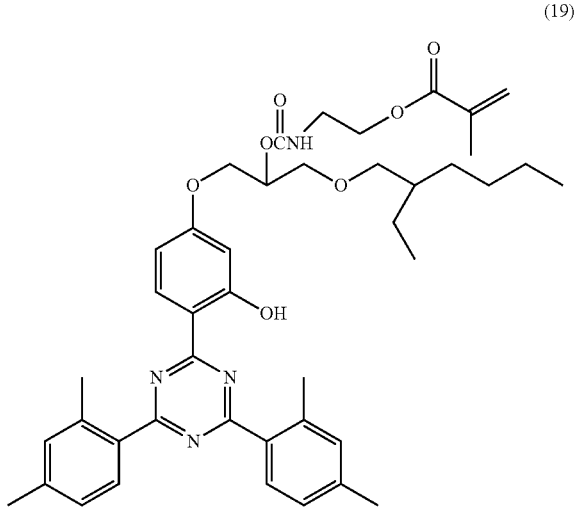

Reference Example 2

(Polymer Having UV Absorbing Groups and Acryloxy Groups)

A polymer having UV absorbing groups and acryloxy groups (PolUVA, non-volatile 40%) was prepared by the method of Example 1 of JP-A 2012-031434. PolUVA has a UV absorbing group content of 16%.

Reference Example 3

(Silsesquioxane Having a UV Absorbing Group and Acryloxy Group)

A silsesquioxane having a UV absorbing group and acryloxy group (SiUVA-1, non-volatile 50%) was prepared by the method of Example 1 of JP-A 2012-219102. SiUVA-1 has a UV absorbing group content of 16%.

Reference Example 4

(UV Absorber Having an Alkoxysilyl Group)

A UV absorber having an alkoxysilyl group (SiUVA-2) was prepared by the method of Synthesis Example 3 of JP-A 2010-111715. SiUVA-2 has a UV absorbing group content of 55%.

Reference Example 5

(Hydrolytic Condensate of Acrylic Silane)

A mixture of 142 parts of KBM 5103 (Shin-Etsu Chemical Co., Ltd., acryloyloxypropyltrimethoxysilane), 500 parts of isopropyl alcohol, 0.1 part of methoquinone (hydroquinone monomethylether), 1.0 part of tetramethyl ammonium hydroxide, and 20 parts of deionized water were reacted at 20° C. for 24 hours to prepare colorless, transparent liquid. The liquid is concentrated by vacuum distillation, thereby obtaining a hydrolytic condensate of acrylic silane (5103SQ) which was colorless, transparent liquid. The insoluble matter was 99.3% and has a weight average molecular weight of 1,900.

Reference Example 6

(Organic/Inorganic Hybrid Acrylate or Colloidal Silica Surface Treated with Acrylic Silane)

A mixture of 2.8 parts of KBM 5103 (Shin-Etsu Chemical Co., Ltd., acryloyloxypropyltrimethoxysilane), 95.6 parts (27.4 parts of solids) of methyl ethyl ketone silica sol MEK-ST (Nissan Chemical Industries, Ltd., number average particle size 45 nm, silica concentration 30%), and 0.1 part of deionized water was stirred at 80° C. for 3 hours. Methyl orthoformate, 1.4 parts, was added to the mixture, which was heated and stirred at the same temperature for 1 hour, yielding a dispersion of surface treated silica particles. The dispersion had a solid content of 32% by weight. The silica particles had an average particle size of 45 nm.

Preparation of Coating Compositions

Example 5

A photo-curable coating composition C1 was prepared by blending 1.33 parts of compound S1 obtained in Example 1, 21.1 parts of Aronix M-403 (Toagosei Co., Ltd., dipentaerythritol penta- and hexaacrylate), 3.9 parts of HDDA (Daicel Cytec Co., Ltd., 1,6-hexane diol diacrylate), 0.45 part of IRGACURE 184 (polymerization initiator by BASF, 1-hydroxycyclohexyl phenyl ketone), 0.45 part of LUCILIN TPO (polymerization initiator by BASF, 2,4,6-trimethylbenzoyldiphenylphosphine oxide), 0.17 part of KP341 (Shin-Etsu Chemical Co., Ltd., polyether-modified silicone) as leveling agent, and 30 parts of propylene glycol monomethyl ether.

Examples 6 to 10 and Comparative Examples 1 to 11

As in Example 5, coating compositions C2 to C6 (Examples 6 to 10) and comparative coating compositions R1 to R11 (Comparative Examples 1 to 11) were prepared in accordance with the recipe shown in Tables 1 and 2 and using the UV absorbers of Examples 1 to 4 and Reference Examples 1 to 5 and other UV absorbers. Each of the coating compositions was flow cast to the surface of a polycarbonate sheet of 150 mm×100 mm×5 mm thick (polycarbonate NF-2000 by Mitsubishi Engineering-Plastics Corp.), air dried for 5 minutes, heated at 80° C. for 1 minute, and irradiated under a high-pressure mercury lamp in a dose of 600 mJ/cm², for curing the coating. Test samples were obtained in this way.

Examples 11 to 14

As in Example 5, coating compositions C7 to C10 (Examples 11 to 14) were prepared in accordance with the recipe shown in Table 1 and using the absorbers of Examples 1 to 4. Each of the coating compositions was flow cast to the surface of a polycarbonate sheet of 15 cm×10 cm×5 mm thick (polycarbonate NF-2000 by Mitsubishi Engineering-Plastics Corp.), air dried for 5 minutes, heated at 80° C. for 1 minute, and irradiated under a high-pressure mercury lamp in a dose of 600 mJ/cm², for curing the coating. Test samples were obtained in this way.

The samples or coatings were examined by the following tests.

[Evaluation of Cured Coating]

Appearance

A coating was visually observed to inspect any defects.
○: no defects
Δ: colored
x: foreign matter, uneven, whitened Mar Resistance Using a Taber abrader equipped with an abrasive wheel CS-10F, a sample was tested under a load of 500 g according to ASTM 1044. After 500 rounds, the sample was measured for haze (Hz). A haze difference before and after the test is reported as mar resistance.

Initial Adhesion

A cross-hatch adhesion test was performed according to JIS K5400 by scribing a sample with a razor along six spaced 2-mm apart orthogonal lines to define 25 square sections in the coating, closely attaching adhesive tape (Cellotape by Nichiban Co., Ltd.) thereto, and quickly pulling back the tape at 90°. The number of remaining (not peeled) coating sections is expressed as X/25.

Boiling Adhesion

A sample was immersed in boiling water for 2 hours before it was examined for adhesion by the same cross-hatch adhesion test.

Weather Resistance

Using the Eye-Super UV tester W-151 of Iwasaki Electric Co., Ltd., a weathering test in which each cycle consists of [black panel temperature 63° C., humidity 50% RH, irradiance 50 mW/cm$^2$, wet 10 sec/hour, 5 hours] and [black panel temperature 30° C., humidity 95% RH, 1 hour] was repeated for 100, 200 and 300 hours. After the weathering test, the coating was observed for cracks and peels by the naked eyes and under a microscope (magnifying power ×250).
○: no defects
Δ: some cracks or partial peel
x: cracks over the entire coating or entire peel The test results are shown in Tables 1 and 2.

TABLE 1

| | | Example | | | | | | | | | |
|---|---|---|---|---|---|---|---|---|---|---|---|
| | | 5 | 6 | 7 | 8 | 9 | 10 | 11 | 12 | 13 | 14 |
| Formulation | Type | C1 | C2 | C3 | C4 | C5 | C6 | C7 | C8 | C9 | C10 |
| Component (A) | S1 [48%] | 1.33 | | | | 3.99 | | 5.32 | | 3.99 | 3.99 |
| | S2 [44%] | | 1.33 | | | | | | | | |
| | S3 [41%] | | | 1.33 | | | | | | | |
| | S4 [43%] | | | | 1.33 | | 3.99 | | 5.32 | | |
| Component (B) | A-M403 | 21.1 | 21.1 | 21.1 | 21.1 | 21.1 | 21.1 | | | 5.0 | |
| | HDDA | 3.9 | 3.9 | 3.9 | 3.9 | 3.9 | 3.9 | 3.5 | 3.5 | 2.0 | 2.0 |
| | U-4HA | 3.9 | 3.9 | 3.9 | 3.9 | 3.9 | 3.9 | 21.5 | 21.5 | 14.5 | 14.5 |
| | 5103SQ | | | | | | | | | 5.0 | 10.0 |
| | Silica | | | | | | | 2.5 | 2.5 | 2.5 | 2.5 |
| Component (C) | I184 | 0.45 | 0.45 | 0.45 | 0.45 | 0.45 | 0.45 | 0.45 | 0.45 | 0.45 | 0.45 |
| | L-TPO | 0.45 | 0.45 | 0.45 | 0.45 | 0.45 | 0.45 | 0.45 | 0.45 | 0.45 | 0.45 |
| Additive | KP-341 | 0.17 | 0.17 | 0.17 | 0.17 | 0.17 | 0.17 | 0.17 | 0.17 | 0.17 | 0.17 |
| Solvent | PGM | 30 | 30 | 30 | 30 | 30 | 30 | 30 | 30 | 30 | 30 |
| Total | | 61.3 | 61.3 | 61.3 | 61.3 | 64.0 | 64.0 | 63.9 | 63.9 | 64.0 | 64.0 |
| Evaluation of coating | | | | | | | | | | | |
| Coating appearance | | ○ | ○ | ○ | ○ | ○ | ○ | ○ | ○ | ○ | ○ |
| Initial Hz | | 0.68 | 0.73 | 0.77 | 0.82 | 0.73 | 0.88 | 0.84 | 0.81 | 0.72 | 0.80 |
| Mar resistance | | 5.4 | 5.5 | 4.9 | 4.1 | 5.9 | 4.0 | 5.7 | 5.1 | 3.8 | 3.2 |
| Initial adhesion | | 25 | 25 | 25 | 25 | 25 | 25 | 25 | 25 | 25 | 25 |
| Boiling adhesion | | 25 | 25 | 25 | 25 | 25 | 25 | 25 | 25 | 25 | 25 |
| Weather resistance | 100 hr | ○ | ○ | ○ | ○ | ○ | ○ | ○ | ○ | ○ | ○ |
| | 200 hr | ○ | ○ | ○ | ○ | ○ | ○ | ○ | ○ | ○ | ○ |
| | 300 hr | x peeled | x peeled | x peeled | x peeled | ○ | ○ | ○ | ○ | ○ | ○ |

For component (A), the value in brackets [ ] is a UV absorbing group content.

TABLE 2

| | | Comparative Example | | | | | | |
|---|---|---|---|---|---|---|---|---|
| Formulation | Type | 1 R1 | 2 R2 | 3 R3 | 4 R4 | 5 R5 | 6 R6 | 7 R7 |
| UVA | R93 [65%] | 1.33 | | | | | | 3.99 |
| | T405 [67%] | | 1.33 | | | | | |
| | T479 [72%] | | | 1.56 (1.33) | | | | |
| | T405M0I [53%] | | | | 1.33 | | | |
| | PolUVA [16%] | | | | | 2.66 (1.33) | | |

TABLE 2-continued

|  |  |  |  |  |  |  |  |  |
|---|---|---|---|---|---|---|---|---|
|  | SiUVA-1 [16%] |  |  |  |  |  | 3.33 (1.33) |  |
|  | SiUVA-2 [55%] |  |  |  |  |  |  |  |
| Component (B) | A-M403 | 21.1 | 21.1 | 21.1 | 21.1 | 21.1 | 21.1 | 21.1 |
|  | HDDA | 3.9 | 3.9 | 3.9 | 3.9 | 3.9 | 3.9 | 3.9 |
| Component (C) | I184 | 0.45 | 0.45 | 0.45 | 0.45 | 0.45 | 0.45 | 0.45 |
|  | L-TPO | 0.45 | 0.45 | 0.45 | 0.45 | 0.45 | 0.45 | 0.45 |
| Additive | KP-341 | 0.17 | 0.17 | 0.17 | 0.17 | 0.17 | 0.17 | 0.17 |
| Solvent | PGM | 30 | 30 | 30 | 30 | 30 | 30 | 30 |
| Total |  | 57.4 | 57.4 | 57.6 | 57.4 | 58.7 | 59.4 | 60.1 |

Evaluation of coating

|  |  |  |  |  |  |  |  |  |
|---|---|---|---|---|---|---|---|---|
| Coating appearance |  | ○ | ○ | ○ | ○ | ○ | ○ | x whitened |
| Initial Hz |  | 0.32 | 0.45 | 0.75 | 0.71 | 0.93 | 0.62 |  |
| Mar resistance |  | 7.1 | 8.3 | 7.2 | 6.4 | 10.3 | 9.1 |  |
| Initial adhesion |  | 25 | 25 | 25 | 25 | 25 | 25 |  |
| Boiling adhesion |  | 25 | 25 | 25 | 25 | 25 | 25 |  |
| Weather resistance | 100 hr | ○ | ○ | ○ | ○ | ○ | ○ |  |
|  | 200 hr | x peeled | x peeled | x peeled | x peeled | x peeled | x peeled |  |
|  | 300 hr |  |  |  |  |  |  |  |

|  |  | Comparative Example |  |  |  |
|---|---|---|---|---|---|
| Formulation |  | 8 | 9 | 10 | 11 |
| Type |  | R8 | R9 | R10 | R11 |
| UVA | R93 [65%] |  |  |  |  |
|  | T405 [67%] |  |  |  |  |
|  | T479 [72%] |  |  |  |  |
|  | T405M0I [53%] | 3.99 |  |  |  |
|  | PolUVA [16%] |  | 7.98 (3.99) |  |  |
|  | SiUVA-1 [16%] |  |  |  |  |
|  | SiUVA-2 [55%] |  |  |  | 3.99 |
| Component (B) | A-M403 | 21.1 | 21.1 | 21.1 | 21.1 |
|  | HDDA | 3.9 | 3.9 | 3.9 | 3.9 |
| Component (C) | I184 | 0.45 | 0.45 | 0.45 | 0.45 |
|  | L-TPO | 0.45 | 0.45 | 0.45 | 0.45 |
| Additive | KP-341 | 0.17 | 0.17 | 0.17 | 0.17 |
| Solvent | PGM | 30 | 30 | 30 | 30 |
| Total |  | 60.1 | 64.1 | 56.1 | 60.1 |

Evaluation of coating

|  |  |  |  |  |  |
|---|---|---|---|---|---|
| Coating appearance |  | ○ | ○ | ○ | Δ yellow |
| Initial Hz |  | 0.97 | 1.77 | 0.25 | 0.63 |
| Mar resistance |  | 13.1 | 16.5 | 5.7 | 12.8 |
| Initial adhesion |  | 25 | 25 | 25 | 25 |
| Boiling adhesion |  | 25 | 25 | 25 | 25 |
| Weather resistance | 100 hr | ○ | ○ | x peeled | ○ |
|  | 200 hr | ○ | ○ |  | x peeled |
|  | 300 hr | x peeled | x peeled |  |  |

For UVA, the value in brackets [ ] is a UV absorbing group content; and the value in parentheses ( ) is an amount (in parts) calculated as solids.

The abbreviations in Tables 1 and 2 are as follows.
Component (B)
  A-M403: dipentaerythritol penta- and hexaacrylate available under the trade name Aronix M403 from Toagosei Co., Ltd.
  HDDA: 1,6-hexane diol diacrylate available under the trade name HDDA from Daicel-Allnex Ltd.
  U-4HA: urethane acrylate of non-yellowing type available under the trade name U-4HA from Shin-Nakamura Chemical Co., Ltd.

5103SQ: hydrolytic condensate of KBM 5103 (Shin-Etsu Chemical Co., Ltd., acryloyloxypropyltrimethoxysilane)

Silica: dispersion of organic/inorganic hybrid acrylate or silica particles surface treated with acryloyloxypropyltrimethoxysilane available under the trade name KBM-5103 from Shin-Etsu Chemical Co., Ltd.

Component (C)

I184: 1-hydroxycyclohexyl phenyl ketone available under the trade name IRGACURE 184 from BASF L-TPO: 2,4,6-trimethylbenzoyldiphenylphosphine oxide available under the trade name L-TPO from BASF Additive KP341: polyether-modified silicone available under the trade name KP-341 from Shin-Etsu Chemical Co., Ltd.

Solvent

PGM: propylene glycol monomethyl ether

Other UV Absorber

R93: 2-(2'-hydroxy-5'-methacryloxyethylphenyl)-2H-benzotriazole available under the trade name RUVA-93 from Otsuka Chemical Co., Ltd., UV absorbing group content (calculated)=65%

T405: 2-[4-[(2-hydroxy-3-(2'-ethyl)hexyl)oxy]-2-hydroxyphenyl]-4,6-bis(2,4-dimethylphenyl)-1,3,5-triazine available under the trade name Tinuvin 405 from BASF, UV absorbing group content (calculated)=67%

T479: 2-[2-hydroxy-4-(1-octyloxycarbonylethoxy)phenyl]-4,6-bis(4-phenylphenyl)-1,3,5-triazine available under the trade name Tinuvin 405 from BASF, UV absorbing group content (calculated)=72%

T405MOI: the addition reaction product of Tinuvin 405 and Karenz MOI, obtained in Reference Example 1

PolUVA: the polymer having UV absorbing groups and acryloxy groups, obtained in Reference Example 2

SiUVA-1: the silsesquioxane having UV absorbing group and acryloxy group, obtained in Reference Example 3

SiUVA-2: UV absorber having alkoxysilyl group, obtained in Reference Example 4

As compared with the UV absorber-free coating R10 of Comparative Example 10, the coatings C1 to C4 of Examples 5 to 8 maintain an equivalent level of mar resistance and are improved in weather resistance. Also, the coatings C5 to C10 of Examples 9 to 14 wherein the amount of reactive UV absorber is increased maintain mar resistance and are further improved in weather resistance, in comparison with R10. The coatings C9 and C10 of Examples 13 and 14 in which the hydrolytic condensate of acryloyl group-containing alkoxysilane (5103SQ) was incorporated have improved mar resistance as compared with the coating C5 of Example 9 in which the hydrolytic condensate was not incorporated. In contrast, the coatings R2 and R3 of Comparative Examples 2 and 3 using UV absorbers free of a reactive group show a lowering of mar resistance despite an improvement in weather resistance, in comparison with R10. The coatings R2 and R3 are somewhat inferior in weather resistance to the coatings C1 to C4. This is presumably because the UV absorber is not incorporated in the binder. The coatings R1 and R4 of Comparative Examples 1 and 4 using the UV absorber having one reactive group are poorer in mar resistance and weather resistance than C1. This is also true for the coatings R5 and R6 of Comparative Examples 5 and 6 using polymeric UV absorber and UV-absorbing silsesquioxane. Further, the coatings R7, R8 and R9 of Comparative Examples 7, 8 and 9 wherein the amount of UV absorber is increased show drawbacks like whitened coating and a drastic drop of mar resistance. The coating R11 of Comparative Example 11 using the UV absorber having alkoxysilyl group is colored yellow and poorer in mar resistance and weather resistance than the coatings C5 and C6 of Examples 9 and 10. These results demonstrate the advantages of the reactive UV absorbers of the invention.

Example 15

Figure 4:
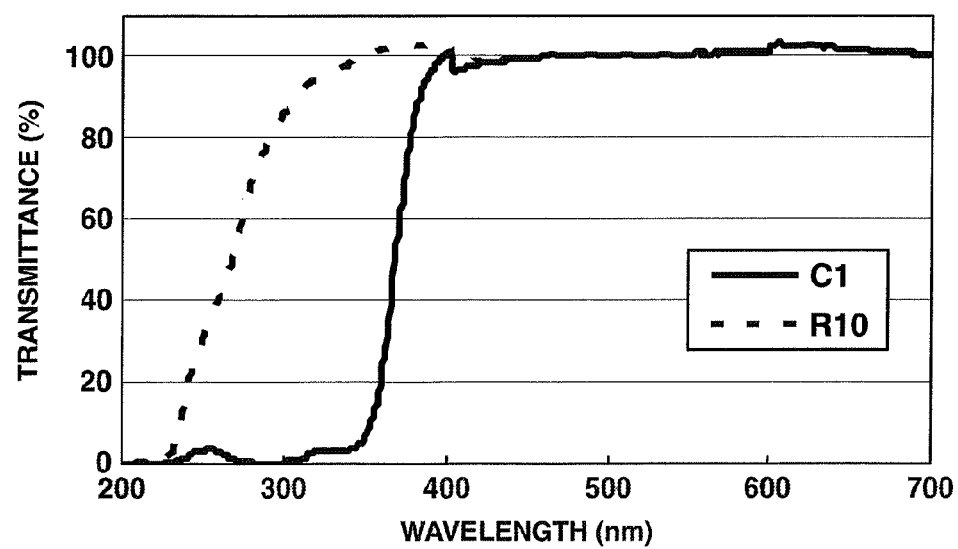
FIG. 4 is a diagram showing the transmission spectrum of a coating obtained in Example 13.

Each of coating compositions C1 and R10 of Example 5 and Comparative Example 10 was flow cast to the surface of a quart glass plate of 40 mm×10 mm×1 mm thick, air dried for 5 minutes, and irradiated under a high-pressure mercury lamp in a dose of 600 mJ/cm$^2$ for curing the coating. The cured coatings were analyzed by spectroscopy, obtaining the transmission spectra of FIG. 4. The coating of composition C1 absorbs UV in the wavelength range of at least 300 nm whereas the coating of composition R10 is not effective for absorbing UV of at least 300 nm.

A coating resulting from a coating composition comprising a reactive UV absorber according to the invention shows a drastically increased UV absorbing capacity, which is effective for significantly retarding deterioration of polycarbonate resin of which substrates are made. This suppresses development of defects after the weathering test. In particular, an improvement in peel resistance is outstanding.

Japanese Patent Application No. 2013-075713 is incorporated herein by reference.

Although some preferred embodiments have been described, many modifications and variations may be made thereto in light of the above teachings. It is therefore to be understood that the invention may be practiced otherwise than as specifically described without departing from the scope of the appended claims.

The invention claimed is:

1. A coated article comprising
 a substrate, and
 a cured coating of a coating composition coated on the substrate directly or via at least one other layer,
 wherein said coating composition comprises a reactive UV absorber and a binder precursor,
 wherein said reactive UV absorber has the general formula (1):

$$O-X-(T-Q-(P)_m)_n \quad (1)$$

(with OH, triazine ring structure as shown)

wherein $Y^1$ and $Y^2$ are each independently a substituent group of the general formula (2):

(2) (phenyl-phenyl structure with $R^1$, $R^2$, $R^3$ substituents and repeat unit $r$)

wherein * stands for a bonding site, r is 0 or 1, $R^1$, $R^2$ and $R^3$ are each independently selected from the group consisting of hydrogen, hydroxyl, $C_1$-$C_{20}$ alkyl, $C_4$-$C_{12}$ cycloalkyl, $C_2$-$C_{20}$ alkenyl, $C_1$-$C_{20}$ alkoxy, $C_4$-$C_{12}$ cycloalkoxy, $C_2$-$C_{20}$ alkenyloxy, $C_7$-$C_{20}$ aralkyl, halogen, —C≡N, $C_1$-$C_5$ haloalkyl, —SO$_2$R', —SO$_3$H, —SO$_3$M (M=alkali metal), —COOR', —CONHR', —CONR'R", —OCOOR', —OCOR', —OCONHR', (meth)acrylamino, (meth)acryloxy, optionally substituted $C_6$-$C_{12}$ aryl and optionally substituted $C_3$-$C_{12}$ heteroaryl, wherein R' and R" are each independently hydrogen, $C_1$-$C_{20}$ alkyl, $C_4$-$C_{12}$ cycloalkyl, optionally substituted $C_6$-$C_{12}$ aryl or optionally substituted $C_3$-$C_{12}$ heteroaryl, X is a group having the general formula (3) or (4):

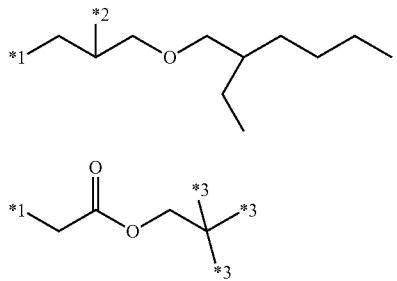

(3)

(4)

wherein *1 bonds to the oxygen in formula (1), *2 bonds to T in formula (1), *3 each independently is hydrogen or bonds to T in formula (1) directly or via a divalent, linear or branched, saturated hydrocarbon group which may be separated by at least one element of oxygen, nitrogen, sulfur, and phosphor, at least one *3 bonds to T directly or via a divalent, linear or branched, saturated hydrocarbon group which may be separated by at least one element of oxygen, nitrogen, sulfur, and phosphor, T is a urethane group —O—(C═O)—NH—, Q is a group having the general formula (5) or (6):

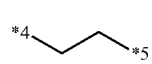

(5)

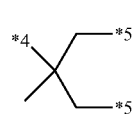

(6)

wherein *4 bonds to T in formula (1), and *5 bonds to P in formula (1),

P is (meth)acryloxy, m is 1 or 2, and n is an integer of 1 to 3, with the proviso that m and n are not equal to 1 at the same time.

2. The coated article of claim 1, wherein the substrate is made of an organic resin or wood.

3. The coated article of claim 1 wherein in formula (1), $R^1$, $R^2$ and $R^3$ are each independently hydrogen or methyl, X is a group of formula (3), Q is a group of formula (6), m is 2, and n is 1.

* * * * *